(12) United States Patent
Ma et al.

(10) Patent No.: US 10,287,569 B2
(45) Date of Patent: May 14, 2019

(54) ENZYME FOR BIOSYNTHESIS OF ISOPRENE AND ISOPENTENYL, AND MUTANT THEREOF

(71) Applicant: INSTITUTE OF MICROBIOLOGY, CHINESE ACADEMY OF SCIENCES, Beijing (CN)

(72) Inventors: Yanhe Ma, Beijing (CN); Deyong Ge, Beijing (CN); Yanfen Xue, Beijing (CN)

(73) Assignee: Institute of Microbiology, Chinese Academy of Sciences, Beijing (CN)

( * ) Notice: Subject to any disclaimer, the term of this patent is extended or adjusted under 35 U.S.C. 154(b) by 0 days.

(21) Appl. No.: 15/578,767

(22) PCT Filed: Feb. 4, 2016

(86) PCT No.: PCT/CN2016/073413
§ 371 (c)(1),
(2) Date: Dec. 1, 2017

(87) PCT Pub. No.: WO2017/132924
PCT Pub. Date: Aug. 10, 2017

(65) Prior Publication Data
US 2018/0087040 A1    Mar. 29, 2018

(51) Int. Cl.
| | | |
|---|---|---|
| *C12N 9/88* | (2006.01) | |
| *C07K 14/32* | (2006.01) | |
| *C12P 5/00* | (2006.01) | |
| *C12P 5/02* | (2006.01) | |

(52) U.S. Cl.
CPC ............... *C12N 9/88* (2013.01); *C07K 14/32* (2013.01); *C12P 5/007* (2013.01); *C12P 5/026* (2013.01); *C12Y 402/03027* (2013.01)

(58) Field of Classification Search
CPC .......................... C12N 9/88; C12Y 402/03027

USPC .......................................................... 435/221
See application file for complete search history.

(56) References Cited

U.S. PATENT DOCUMENTS

| | | |
|---|---|---|
| 8,288,148 B2 | 10/2012 | Cervin et al. |
| 8,686,702 B2 | 4/2014 | Muir et al. |
| 8,709,785 B2 | 4/2014 | Cervin et al. |
| 8,993,305 B2 | 3/2015 | Beck et al. |
| 9,260,727 B2 | 2/2016 | Cervin et al. |
| 2009/0203102 A1 | 8/2009 | Cervin et al. |
| 2012/0164711 A1 | 6/2012 | Muir et al. |
| 2013/0071908 A1 | 3/2013 | Cervin et al. |
| 2013/0078699 A1 | 3/2013 | Cervin et al. |
| 2013/0089906 A1 | 4/2013 | Beck et al. |

FOREIGN PATENT DOCUMENTS

| | | |
|---|---|---|
| CN | 103476926 A | 12/2013 |
| CN | 104053765 A | 9/2014 |
| WO | 2009076676 A2 | 6/2009 |

OTHER PUBLICATIONS

International Search Report from corresponding PCT Application No. PCT/CN2016/073413 dated Oct. 23, 2016.
"4-hydroxy-3-methylbut-2-enyl diphosphate reductase [Bacillus cellulosilyticus]", GENBANK Accession No. WP_013488222.1 (May 26, 2013).

*Primary Examiner* — Tekchand Saidha
(74) *Attorney, Agent, or Firm* — Abelman, Frayne & Schwab

(57) ABSTRACT

The invention provides a polypeptide capable of using 4-hydroxy-3-methyl-but-2-enyl pyrophosphate (HMBPP) as a substrate to produce isoprene, a nucleic acid encoding the polypeptide, and a vector and a cell comprising the nucleic acid. In addition, the invention also provides a method for producing isoprene using the polypeptide, and a method for preparing the polypeptide.

19 Claims, 8 Drawing Sheets
Specification includes a Sequence Listing.

SEQUENCE LISTING

<160> NUMBER OF SEQ ID NOS: 10

<210> SEQ ID NO 1
<211> LENGTH: 957
<212> TYPE: DNA
<213> ORGANISM: Bacillus sp. N16-5

<400> SEQUENCE: 1

```
atggaggttt tgaaaatttc cccacggggt tattgttacg gcgtggtaga tgctatggtt      60
atggctaaac aagctgctga aaatccagat ttaccacggc ctatctatat attaggaatg     120
attgttcaca ataaacatgt gacagatgcc tttgatgaag agggtattat cacgcttgac     180
ggtccaaaca gattagagat tattaagcaa gttgataaag gaaccgttat ttttacggca     240
catggcgttt cgccagaagt acgaactatc gctaaagaaa aaggattaac gacgatcgat     300
gccacatgtc cagatgtaac cgtcactcac gacctaattc gaaataaaat ggaagaggggc     360
```

-continued

```
tacgagttta tctacattgg taagaaagga cacccccgagc cagaaggcgc tatcggtgtt    420
gctccagaca ttgtttattt agtagaaaat gttgaagatg tagaaagact tcagctgaaa    480
ggcaataaaa ttcttataac aaaccagacg acaatgagtc aatgggatgt ctctcacatc    540
attaaagctg cgaaaaacaa ataccctgaa gcagaggtcc ataacgaaat ttgcatggct    600
actcaagttc gtcaagaagc tgttgctgaa caagctggag aagctgattt actaattgtt    660
gtgggtgatc cgaaaagtaa taactctaat cgtctcgcac aagtatcgat ggacattacc    720
ggaacacctg cctacagaat agcaaatgtt aatgaactca atcttgaatg gcttaaaggg    780
atcaaaaaag tggcagtcac tgctggggct agcacaccca ctcctgttac aaaagaagtg    840
attgctttca tcgaaaagtt taatgaagat gaccccaca catgggatac gacgagtact    900
gttaaattaa caaaaattct ccctaaagtg agaaagaaaa aagcggagcg ggcctaa      957
```

<210> SEQ ID NO 2
<211> LENGTH: 318
<212> TYPE: PRT
<213> ORGANISM: Bacillus sp. N16-5

<400> SEQUENCE: 2

```
Met Glu Val Leu Lys Ile Ser Pro Arg Gly Tyr Cys Tyr Gly Val Val
1               5                   10                  15

Asp Ala Met Val Met Ala Lys Gln Ala Ala Glu Asn Pro Asp Leu Pro
                20                  25                  30

Arg Pro Ile Tyr Ile Leu Gly Met Ile Val His Asn Lys His Val Thr
            35                  40                  45

Asp Ala Phe Asp Glu Glu Gly Ile Ile Thr Leu Asp Gly Pro Asn Arg
        50                  55                  60

Leu Glu Ile Ile Lys Gln Val Asp Lys Gly Thr Val Ile Phe Thr Ala
65                  70                  75                  80

His Gly Val Ser Pro Glu Val Arg Thr Ile Ala Lys Glu Lys Gly Leu
                85                  90                  95

Thr Thr Ile Asp Ala Thr Cys Pro Asp Val Thr Val Thr His Asp Leu
            100                 105                 110

Ile Arg Asn Lys Met Glu Glu Gly Tyr Glu Phe Ile Tyr Ile Gly Lys
        115                 120                 125

Lys Gly His Pro Glu Pro Glu Gly Ala Ile Gly Val Ala Pro Asp Ile
    130                 135                 140

Val Tyr Leu Val Glu Asn Val Glu Asp Val Glu Arg Leu Gln Leu Lys
145                 150                 155                 160

Gly Asn Lys Ile Leu Ile Thr Asn Gln Thr Thr Met Ser Gln Trp Asp
                165                 170                 175

Val Ser His Ile Ile Lys Ala Ala Lys Asn Lys Tyr Pro Glu Ala Glu
            180                 185                 190

Val His Asn Glu Ile Cys Met Ala Thr Gln Val Arg Gln Glu Ala Val
        195                 200                 205

Ala Glu Gln Ala Gly Glu Ala Asp Leu Leu Ile Val Val Gly Asp Pro
    210                 215                 220

Lys Ser Asn Asn Ser Asn Arg Leu Ala Gln Val Ser Met Asp Ile Thr
225                 230                 235                 240

Gly Thr Pro Ala Tyr Arg Ile Ala Asn Val Asn Glu Leu Asn Leu Glu
                245                 250                 255

Trp Leu Lys Gly Ile Lys Lys Val Ala Val Thr Ala Gly Ala Ser Thr
            260                 265                 270
```

```
Pro Thr Pro Val Thr Lys Glu Val Ile Ala Phe Ile Glu Lys Phe Asn
            275                 280                 285

Glu Asp Asp Pro His Thr Trp Asp Thr Thr Ser Thr Val Lys Leu Thr
            290                 295                 300

Lys Ile Leu Pro Lys Val Arg Lys Lys Ala Glu Arg Ala
305                 310                 315

<210> SEQ ID NO 3
<211> LENGTH: 318
<212> TYPE: PRT
<213> ORGANISM: Artificial
<220> FEATURE:
<223> OTHER INFORMATION: Mutant protein H131N

<400> SEQUENCE: 3

Met Glu Val Leu Lys Ile Ser Pro Arg Gly Tyr Cys Tyr Gly Val Val
1               5                   10                  15

Asp Ala Met Val Met Ala Lys Gln Ala Ala Glu Asn Pro Asp Leu Pro
            20                  25                  30

Arg Pro Ile Tyr Ile Leu Gly Met Ile Val His Asn Lys His Val Thr
            35                  40                  45

Asp Ala Phe Asp Glu Glu Gly Ile Ile Thr Leu Asp Gly Pro Asn Arg
        50                  55                  60

Leu Glu Ile Ile Lys Gln Val Asp Lys Gly Thr Val Ile Phe Thr Ala
65                  70                  75                  80

His Gly Val Ser Pro Glu Val Arg Thr Ile Ala Lys Glu Lys Gly Leu
                85                  90                  95

Thr Thr Ile Asp Ala Thr Cys Pro Asp Val Thr Val Thr His Asp Leu
            100                 105                 110

Ile Arg Asn Lys Met Glu Glu Gly Tyr Glu Phe Ile Tyr Ile Gly Lys
        115                 120                 125

Lys Gly Asn Pro Glu Pro Glu Gly Ala Ile Gly Val Ala Pro Asp Ile
        130                 135                 140

Val Tyr Leu Val Glu Asn Val Glu Asp Val Glu Arg Leu Gln Leu Lys
145                 150                 155                 160

Gly Asn Lys Ile Leu Ile Thr Asn Gln Thr Thr Met Ser Gln Trp Asp
                165                 170                 175

Val Ser His Ile Ile Lys Ala Ala Lys Asn Lys Tyr Pro Glu Ala Glu
            180                 185                 190

Val His Asn Glu Ile Cys Met Ala Thr Gln Val Arg Gln Glu Ala Val
        195                 200                 205

Ala Glu Gln Ala Gly Glu Ala Asp Leu Leu Ile Val Val Gly Asp Pro
        210                 215                 220

Lys Ser Asn Asn Ser Asn Arg Leu Ala Gln Val Ser Met Asp Ile Thr
225                 230                 235                 240

Gly Thr Pro Ala Tyr Arg Ile Ala Asn Val Asn Glu Leu Asn Leu Glu
                245                 250                 255

Trp Leu Lys Gly Ile Lys Lys Val Ala Val Thr Ala Gly Ala Ser Thr
            260                 265                 270

Pro Thr Pro Val Thr Lys Glu Val Ile Ala Phe Ile Glu Lys Phe Asn
        275                 280                 285

Glu Asp Asp Pro His Thr Trp Asp Thr Thr Ser Thr Val Lys Leu Thr
        290                 295                 300

Lys Ile Leu Pro Lys Val Arg Lys Lys Ala Glu Arg Ala
305                 310                 315
```

```
<210> SEQ ID NO 4
<211> LENGTH: 318
<212> TYPE: PRT
<213> ORGANISM: Artificial
<220> FEATURE:
<223> OTHER INFORMATION: Mutant protein E133Q

<400> SEQUENCE: 4

Met Glu Val Leu Lys Ile Ser Pro Arg Gly Tyr Cys Tyr Gly Val Val
1               5                   10                  15

Asp Ala Met Val Met Ala Lys Gln Ala Ala Glu Asn Pro Asp Leu Pro
            20                  25                  30

Arg Pro Ile Tyr Ile Leu Gly Met Ile Val His Asn Lys His Val Thr
        35                  40                  45

Asp Ala Phe Asp Glu Glu Gly Ile Ile Thr Leu Asp Gly Pro Asn Arg
    50                  55                  60

Leu Glu Ile Ile Lys Gln Val Asp Lys Gly Thr Val Ile Phe Thr Ala
65                  70                  75                  80

His Gly Val Ser Pro Glu Val Arg Thr Ile Ala Lys Glu Lys Gly Leu
                85                  90                  95

Thr Thr Ile Asp Ala Thr Cys Pro Asp Val Thr Val Thr His Asp Leu
            100                 105                 110

Ile Arg Asn Lys Met Glu Glu Gly Tyr Glu Phe Ile Tyr Ile Gly Lys
        115                 120                 125

Lys Gly His Pro Gln Pro Glu Gly Ala Ile Gly Val Ala Pro Asp Ile
    130                 135                 140

Val Tyr Leu Val Glu Asn Val Glu Asp Val Glu Arg Leu Gln Leu Lys
145                 150                 155                 160

Gly Asn Lys Ile Leu Ile Thr Asn Gln Thr Thr Met Ser Gln Trp Asp
                165                 170                 175

Val Ser His Ile Ile Lys Ala Ala Lys Asn Lys Tyr Pro Glu Ala Glu
            180                 185                 190

Val His Asn Glu Ile Cys Met Ala Thr Gln Val Arg Gln Glu Ala Val
        195                 200                 205

Ala Glu Gln Ala Gly Glu Ala Asp Leu Leu Ile Val Val Gly Asp Pro
    210                 215                 220

Lys Ser Asn Asn Ser Asn Arg Leu Ala Gln Val Ser Met Asp Ile Thr
225                 230                 235                 240

Gly Thr Pro Ala Tyr Arg Ile Ala Asn Val Asn Glu Leu Asn Leu Glu
                245                 250                 255

Trp Leu Lys Gly Ile Lys Lys Val Ala Val Thr Ala Gly Ala Ser Thr
            260                 265                 270

Pro Thr Pro Val Thr Lys Glu Val Ile Ala Phe Ile Glu Lys Phe Asn
        275                 280                 285

Glu Asp Asp Pro His Thr Trp Asp Thr Thr Ser Thr Val Lys Leu Thr
    290                 295                 300

Lys Ile Leu Pro Lys Val Arg Lys Lys Ala Glu Arg Ala
305                 310                 315

<210> SEQ ID NO 5
<211> LENGTH: 27
<212> TYPE: DNA
<213> ORGANISM: Artificial
<220> FEATURE:
<223> OTHER INFORMATION: Primer
```

```
<400> SEQUENCE: 5
catgccatgg aggttttgaa aatttcc                                         27

<210> SEQ ID NO 6
<211> LENGTH: 33
<212> TYPE: DNA
<213> ORGANISM: Artificial
<220> FEATURE:
<223> OTHER INFORMATION: Primer

<400> SEQUENCE: 6
ccgctcgagt ggcccgctcc gcttttttct ttc                                  33

<210> SEQ ID NO 7
<211> LENGTH: 38
<212> TYPE: DNA
<213> ORGANISM: Artificial
<220> FEATURE:
<223> OTHER INFORMATION: Primer

<400> SEQUENCE: 7
ctacattggt aagaaaggaa accccgagcc agaaggcg                             38

<210> SEQ ID NO 8
<211> LENGTH: 38
<212> TYPE: DNA
<213> ORGANISM: Artificial
<220> FEATURE:
<223> OTHER INFORMATION: Primer

<400> SEQUENCE: 8
cgccttctgg ctcggggttt cctttcttac caatgtag                             38

<210> SEQ ID NO 9
<211> LENGTH: 35
<212> TYPE: DNA
<213> ORGANISM: Artificial
<220> FEATURE:
<223> OTHER INFORMATION: Primer

<400> SEQUENCE: 9
gtaagaaagg acaccccag ccagaaggcg ctatc                                 35

<210> SEQ ID NO 10
<211> LENGTH: 35
<212> TYPE: DNA
<213> ORGANISM: Artificial
<220> FEATURE:
<223> OTHER INFORMATION: Primer

<400> SEQUENCE: 10
gatagcgcct tctggctggg ggtgtccttt cttac                                35
```

ENZYME FOR BIOSYNTHESIS OF ISOPRENE AND ISOPENTENYL, AND MUTANT THEREOF

RELATED APPLICATION

This application is a national phase of international Application No. PCT/CN2016/073413 filed Feb. 4, 2016, incorporated by reference in its entirety.

TECHNICAL FIELD

The invention relates to the technical field of molecular biology, particularly, the field of biosynthesis of isoprene. In particular, the invention provides a polypeptide capable of using 4-hydroxy-3-methyl-but-2-enyl pyrophosphate (HMBPP) as a substrate to produce isoprene, a nucleic acid encoding the polypeptide, a vector and a cell comprising the nucleic acid. In addition, the invention also provides a method for producing isoprene using the polypeptide, and a method for preparing the polypeptide.

BACKGROUND ART

Isoprene is an important chemical material, which is mainly used in the production of rubber, and may also be used in the synthesis of fine chemicals (e.g., isopentenyl chloride, coriandrol, laurene and Vitamin A, E, K, etc.). Now, almost all the isoprene and isoamylene in industrial application are derived from petroleum derived materials. However, with the increasing demand for isoprene in industry and the gradual depletion of petroleum resources in the world, it is urgent to develop an alternative source for isoprene production. In this background, for the advantages such as no pollution and being reproducible, biosynthesis of isoprene has drawn a widely public attention and been studied, and preliminary progress has been achieved. In 2010, Genencor Co. and Goodyear Co. worked together and developed a method for biosynthesis of isoprene, the essential of which resides in constructing an engineered bacterium, which can be utilized to convert reproducible saccharides to isoprene; and the yield of isoprene produced by the method reached 60 g/L.

The existing studies show that isoprene is synthesized in organism mainly by the following pathways: the precursor of isoprene, dimethylallyl pyrophosphate (DMAPP), is first synthesized by metabolic pathway, and DMAPP is then converted to isoprene in the presence of isoprene synthase (IspS; EC 4.2.3.27) as a catalyst. DMAPP and its isomer isopentenyl pyrophosphate (IPP) are the precursors for all the isoprene compounds discovered now, and can be synthesized by two different pathways in organism: DXP pathway and MVA pathway. DXP pathway comprises, firstly producing 1-deoxy-D-xylulose 5-phosphate (DXP) by condensation of pyruvate and glyceraldehyde 3-phosphate; then converting DXP to 4-hydroxy-3-methyl-but-2-enyl pyrophosphate (HMBPP) through five enzyme reactions; and then in the presence of HMBPP reductase (IspH), converting HMBPP to DMAPP and IPP. MVA pathway uses acetyl CoA as a single raw material, and produces DMAPP through 7 continuous enzyme reactions. Detailed introduction on the biosynthesis of isoprene (particularly DXP pathway and MVA pathway) can be found in, for example, Tomohisa Kuzuyama, Biosci. Biotechnol. Biochem., 66(8), 1619-1627, 2002; Thomas D. Sharkey et al, Plant Physiology, February 2005, Vol. 137, pp. 700-712; and U.S. Pat. No. 8,507,235B2.

It is generally believed that isoprene synthase (IspS; EC 4.2.3.27) is an enzyme involved in the last step of biosynthesis of isoprene. Now, a plant-derived IspS has been isolated and identified. The enzyme uses DMAPP as a substrate, and produces isoprene by catalyzing the removal of pyrophosphate group from the substrate. Although IspS is present in many plants, they have a high homology, and a relatively large Km value that reaches the level of mM. In addition, it is also found in studies that a high-concentration accumulation of the substrate (DMAPP and IPP) of IspS in a cell is toxic to the growth of engineering bacteria. Thus, the method for biosynthesis of isoprene using IspS still has shortcomings.

Therefore, there is a demand for developing a new method for biosynthesis of isoprene in the art.

BACKGROUND ART

The inventor discovered a new enzyme in alkaliphilic *Bacillus* sp. N16-5 (*Bacillus* sp. N16-5), which has several activities, including: (a) the activity of using HMBPP as a substrate to produce DMAPP and IPP; (b) the activity of using HMBPP as a substrate to produce isoprene; and (c) the activity of using DMAPP as a substrate to produce isoamylene (2-methyl-2-butene and 3-methyl-1-butene). Furthermore, the inventor obtained two mutants (H131N and E133Q) by modifying the enzyme. The two mutants lose the activity of using HMBPP as a substrate to produce DMAPP and IPP and the activity of producing isoamylene, but retain the activity of using HMBPP as a substrate to produce isoprene, and have a stronger capability of producing isoprene in a cell than that of the wild-type enzyme (having the yield of isoprene increased by 3-4 folds). On the basis of the above, the inventor develops new methods for synthesis of isoprene and isoamylene.

Therefore, in one aspect, the invention provides a polypeptide, which has an activity of using 4-hydroxy-3-methyl-but-2-enyl pyrophosphate (HMBPP) as a substrate to produce isoprene, and has an amino acid sequence selected from the group consisting of:

(1) an amino acid sequence set forth in SEQ ID NO: 2;

(2) an amino acid sequence having an identity of at least 90% with SEQ ID NO: 2; and (3) an amino acid sequence that differs from SEQ ID NO: 2 by substitution, deletion or addition of one or more amino acid residues.

In some preferred embodiments, the polypeptide according to the invention has an amino acid sequence having an identity of at least 90%, preferably an identity of at least 91%, an identity of at least 92%, an identity of at least 93%, an identity of at least 94%, an identity of at least 95%, an identity of at least 96%, an identity of at least 97%, an identity of at least 98%, or an identity of at least 99% with SEQ ID NO: 2.

In some preferred embodiments, the polypeptide according to the invention has an amino acid sequence that differs from SEQ ID NO: 2 by substitution, deletion or addition of one or more (e.g., 1, 2, 3, 4, 5, 6, 7, 8 or 9) amino acid residues.

In some preferred embodiments, the polypeptide according to the invention has an amino acid sequence that differs from SEQ ID NO: 2 by conservative substitution of one or more (e.g., 1, 2, 3, 4, 5, 6, 7, 8 or 9) amino acid residues.

In some preferred embodiments, the polypeptide according to the invention has an amino acid sequence that is SEQ ID NO: 2 or differs from SEQ ID NO: 2 by substitution of one or more (e.g., 1) amino acid residues. For example, in some preferred embodiments, the polypeptide according to the invention has an amino acid sequence that differs from SEQ ID NO: 2 by amino acid substitution at position 131 or 133 of SEQ ID NO: 2. In some preferred embodiments, the polypeptide according to the invention has an amino acid sequence that differs from SEQ ID NO: 2 by mutation of histidine to asparagine at position 131 of SEQ ID NO: 2, or by mutation of glutamic acid to glutamine at position 133 of SEQ ID NO: 2.

In some preferred embodiments, the polypeptide according to the invention has an amino acid sequence selected from the group consisting of SEQ ID NOs: 2, 3 and 4.

In some preferred embodiments, the polypeptide according to the invention has an activity of using dimethylallyl pyrophosphate (DMAPP) as a substrate to produce 2-methyl-2-butene and 3-methyl-1-butene.

In some preferred embodiments, the polypeptide according to the invention does not have an activity of using dimethylallyl pyrophosphate (DMAPP) as a substrate to produce 2-methyl-2-butene and 3-methyl-1-butene.

In another aspect, the invention provides an isolated nucleic acid, encoding the polypeptide as described above. In another aspect, the invention provides a vector, comprising the isolated nucleic acid. In some preferred embodiments, the isolated nucleic acid according to the invention encodes a polypeptide having an amino acid sequence selected from the group consisting of SEQ ID NOs: 2, 3 and 4. Vectors useful for inserting a polynucleotide of interest are well known in the art. In an embodiment, the vector, for example, is a plasmid, a cosmid, a phage, etc.

In another aspect, the invention further relates to a host cell comprising the isolated nucleic acid or the vector. The host cell includes, but is not limited to a prokaryotic cell such as *E. coli* cell and *bacillus* cell (e.g., *Bacillus alcalophilus, Bacillus subtilis*), and a eukaryotic cell such as a yeast cell, an insect cell, a plant cell and an animal cell.

In some preferred embodiments, the isolated nucleic acid is heterogenous relative to the cell. In some preferred embodiments, the isolated nucleic acid is exogenous relative to the cell.

In some preferred embodiments, the cell further comprises a nucleic acid encoding an electron transporter (e.g., ferredoxin) and/or an enzyme (e.g., ferredoxin reductase) needed for an electron transporter to transport electron, or expresses an electron transporter (e.g., ferredoxin) and/or an enzyme (e.g., ferredoxin reductase) needed for an electron transporter to transport electron. For example, the cell may further comprise a nucleic acid encoding ferredoxin and ferredoxin reductase, or express ferredoxin and ferredoxin reductase. In some preferred embodiments, the electron transporter and/or the enzyme needed for an electron transporter to transport electron is endogenous relative to the cell. In some preferred embodiments, the electron transporter and/or the enzyme needed for an electron transporter to transport electron is exogenous relative to the cell. For example, the ferredoxin and/or ferredoxin reductase is endogenous or exogenous relative to the cell. In some preferred embodiments, the cell further comprises an exogenously introduced nucleic acid encoding ferredoxin, and/or an exogenously introduced nucleic acid encoding ferredoxin reductase. In some preferred embodiments, the ferredoxin reductase is ferredoxin-NADP$^+$ reductase (EC 1.18.1.2).

In some preferred embodiments, the cell further expresses a polypeptide of DXP pathway. Preferably, the polypeptide of DXP pathway is selected from the group consisting of 1-deoxy-D-xylulose-5-phosphate synthase (DXS; EC 2.2.1.7), 1-deoxy-D-xylulose-5-phosphate reductoisomerase (DXR; EC 1.1.1.267), 2-C-methyl-D-erythritol 4-phosphate cytidylyltransferase (MCT; EC 2.7.7.60), 4-(cytidine-5'-diphospho)-2-C-methyl-D-erythritol kinase (CMK; EC 2.7.5.148), 2-C-methyl-D-erythritol 2,4-cyclodiphosphate synthase (MCS; EC 4.6.1.12), 4-hydroxy-3-methyl-2-(E)-butenyl-diphosphate synthase (IspG; EC 1.17.7.1), and any combination thereof. In some preferred embodiments, the polypeptide of DXP pathway is endogenous relative to the cell. In some preferred embodiments, the polypeptide of DXP pathway is exogenous relative to the cell.

In some preferred embodiments, the cell further expresses isoprene synthase (IspS; EC 4.2.3.27). In some preferred embodiments, the cell does not express isoprene synthase (IspS; EC 4.2.3.27).

In some preferred embodiments, the cell is a prokaryotic cell, such as *E. coli* or *Bacillus* spp. or blue-green algae.

In another aspect, the invention further relates to a composition, comprising the polypeptide according to the invention, HMBPP, NADPH or NADH, an electron transporter (e.g., ferredoxin), and an enzyme (e.g., ferredoxin reductase) needed for an electron transporter to transport electron. In some preferred embodiments, the composition comprises the polypeptide, HMBPP, NADPH, ferredoxin and ferredoxin reductase (e.g., ferredoxin-NADP$^+$ reductase). The composition according to the invention is useful in synthesis of isoprene in vitro.

In another aspect, the invention further relates to a composition, comprising a polypeptide having an amino acid sequence set forth in SEQ ID NO: 2, DMAPP, NADPH or NADH, an electron transporter (e.g., ferredoxin), and an enzyme (e.g., ferredoxin reductase) needed for an electron transporter to transport electron. In some preferred embodiments, the composition comprises a polypeptide having an amino acid sequence set forth in SEQ ID NO: 2, DMAPP, NADPH, ferredoxin and ferredoxin reductase (e.g., ferredoxin-NADP$^+$ reductase). The composition according to the invention is useful in synthesis of isoamylene (e.g., 3-methyl-1-butene and/or 2-methyl-2-butene) in vitro.

In another aspect, the invention provides a method for producing isoprene, comprising using the polypeptide according to the invention to convert HMBPP to isoprene.

In some preferred embodiments, the method comprises (a) mixing and incubating (preferably incubating at 20-40° C., e.g., incubating at room temperature or 37° C.) the polypeptide, HMBPP, NADPH or NADH, an electron transporter (e.g., ferredoxin), and an enzyme (e.g., ferredoxin reductase) needed for an electron transporter to transport electron; and (b) collecting isoprene produced in step (a). In some preferred embodiments, in step (a), the polypeptide, HMBPP, NADPH, ferredoxin and ferredoxin reductase (e.g., ferredoxin-NADP$^+$ reductase) are mixed and incubated, for example, incubated at 20-40° C. (e.g., incubated at room temperature or 37° C.), to produce isoprene. In some preferred embodiments, the polypeptide has an amino acid sequence set forth in SEQ ID NO: 3 or 4.

In some preferred embodiments, the method does not involve use of isoprene synthase (IspS: EC 4.2.3.27). In some preferred embodiments, the method is used in production of isoprene in vitro.

In another aspect, the invention provides a method for producing isoprene, comprising (a) culturing a cell expressing the polypeptide according to the invention which is exogenously introduced; and (b) collecting isoprene produced in step (a).

In some preferred embodiments, in step (a), a cell is cultured under conditions suitable, for producing isoprene. For example, in order to promote isoprene production in a cell, the cell may be provided with one or more of the following substances: (1) a culture medium for retaining or promoting cell growth; (2) the substrate of the polypeptide according to the invention, HMBPP; (3) an electron transporter (e.g., ferredoxin); (4) an enzyme (e.g., ferredoxin reductase) needed for an electron transporter to transport electron: and (5) NADPH or NADH.

A variety of suitable culture media for culturing cells are well known by a person skilled in the art, and are commercially available.

In some preferred embodiments, the cell further expresses an electron transporter (e.g., ferredoxin) and/or an enzyme (e.g., ferredoxin reductase) needed for an electron transporter to transport electron. For example, the cell further expresses ferredoxin and ferredoxin reductase. In some preferred embodiments, the electron transporter and/or the enzyme needed for an electron transporter to transport electron is endogenous relative to the cell. In some preferred embodiments, the electron transporter and/or the enzyme needed for an electron transporter to transport electron is exogenous relative to the cell. For example, the ferredoxin and/or ferredoxin reductase may be endogenous or exogenous relative to the cell, in some preferred embodiments, the ferredoxin reductase is ferredoxin-NADP$^+$ reductase (EC 1.18.1.2).

In some cases, the cell naturally expresses ferredoxin and ferredoxin reductase. In such a cell, if is not necessary to exogenously introduce a nucleic acid encoding ferredoxin and ferredoxin reductase. However, it is particularly preferred that in such a cell, a nucleic acid encoding ferredoxin and ferredoxin reductase is further introduced, to increase the expression of ferredoxin and ferredoxin reductase, thereby further enhancing the activity of the polypeptide according to the invention. In some cases, the cell does not express ferredoxin and ferredoxin reductase. In such a cell, it is particularly preferred that a nucleic acid encoding ferredoxin and ferredoxin reductase is introduced, so as to provide a high-efficient electron donor for the polypeptide according to the invention.

In some preferred embodiments, HMBPP may be added to a cell culture medium, so as to provide a substrate for the polypeptide according to the invention. In some preferred embodiments, DXP pathway is established in a cell to promote HMBPP synthesis in the cell, thereby providing a substrate for the polypeptide according to the invention. For example, one or more polypeptides involved in DXP pathway can be expressed in a cell so as to promote. HMBPP synthesis in the cell, thereby providing a substrate for the polypeptide according to the invention.

Therefore, in some preferred embodiments, the cell further expresses a polypeptide of DXP pathway. In some preferred embodiments, the polypeptide of DXP pathway is selected from the group consisting of 1-deoxy-D-xylulose-5-phosphate synthase (DXS; EC 2.2.1.7), 1-deoxy-D-xylulose-5-phosphate reductoisomerase (DXR; EC 1.1.1.267), 2-C-methyl-D-erythritol 4-phosphate cytidylyltransferase (MCT; EC 2.7.7.60), 4-(cytidine-5'-diphospho)-2-C-methyl-D-erythritol kinase (CMK; EC 2.7.1.148), 2-C-methyl-D-erythritol 2,4-cyclodiphosphate synthase (MCS; EC 4.6.1.12), 4-hydroxy-3-methyl-2-(E)-butenyl-diphosphate synthase (IspG; EC 1.17.7.1), and any combination thereof. In some preferred embodiments, the cell expresses one, two, three, four, five or six of said polypeptides of DXP pathways.

In some preferred embodiments, the polypeptide of DXP pathway is endogenous relative to the cell. In some preferred embodiments, the polypeptide of DXP pathway is exogenous relative to the cell.

In some preferred embodiments, the cell further expresses isoprene synthase (IspS; EC 4.2.3.27), In such a cell, isoprene may be biosynthesized by several pathways. In some preferred embodiments, the cell does not express isoprene synthase (IspS; EC 4.2.3.27).

In some preferred embodiments, the cell is selected from the group consisting of a prokaryotic cell such as E. coli cell and bacillus cell (e.g., Bacillus alcalophilus, Bacillus subtilis), and a eukaryotic cell such as a yeast cell, an insect cell, a plant cell and an animal cell. However, it is particularly preferred that the cell is a prokaryotic cell, such as E. coli or Bacillus spp. or blue-green algae.

In some preferred embodiments, the method is used in the biosynthesis of isoprene.

In another aspect, the invention provides a method for producing isoamylene (e.g., 3-methyl-1-butene and/or 2-methyl-2-butene), comprising using a polypeptide having an amino acid sequence set forth in SEQ ID NO: 2, to convert DMAPP to isoamylene.

In some preferred embodiments, the method comprises (a) mixing and incubating the polypeptide, DMAPP, NADPH or NADH, an electron transporter (e.g., ferredoxin) and an enzyme (e.g., ferredoxin reductase) needed for an electron transporter to transport electron; and (b) collecting isoamylene produced in step (a). In some preferred embodiments, in step (a), the polypeptide, DMAPP, NADPH, ferredoxin and ferredoxin reductase (e.g., ferredoxin-NADP$^+$ reductase) are mixed and incubated, for example, incubated at 20-40° C. (e.g., incubated at room temperature or 37° C.), to produce isoamylene. In some preferred embodiments, the method is used in the production of isoamylene in vitro.

In another aspect, the invention provides a method for producing isoamylene (e.g., 3-methyl-1-butene and/or 2-methyl-2-butene), comprising (a) culturing a cell expressing an exogenously introduced polypeptide having an amino acid sequence set forth in SEQ ID NO: 2; and (b) collecting isoamylene produced in step (a).

In some preferred embodiments, in step (a), the cell is cultured under conditions suitable for producing isoamylene (e.g., 3-methyl-1-butene and/or 2-methyl-2-butene). For example, in order to promote isoamylene production in a cell, the cell may be provided with one or more of the following substances: (1) a culture medium for retaining or promoting cell growth; (2) the substrate of the polypeptide according to the invention, DMAPP; (3) an electron transporter (e.g., ferredoxin), (4) an enzyme (e.g., ferredoxin reductase) needed for an electron transporter to transport electron; and (5) NADPH or NADH.

A variety of suitable culture media for culturing cells are well known by a person skilled in the art, and are commercially available.

In some preferred embodiments, the cell further expresses an electron transporter (e.g., ferredoxin) and/or an enzyme (e.g., ferredoxin reductase) needed for an electron transporter to transport electron. For example, the cell further expresses ferredoxin and ferredoxin reductase. In some preferred embodiments, the electron transporter and/or the enzyme needed for an electron transporter to transport electron is endogenous relative to the cell. In some preferred embodiments, the electron transporter and/or the enzyme needed for an electron transporter to transport electron is exogenous relative to the cell. For example, the ferredoxin and/or ferredoxin reductase may be endogenous or exogenous relative to the cell. In some preferred embodiments, the ferredoxin reductase is ferredoxin-NADP$^+$ reductase (EC 1.18.1.2).

In some cases, the cell naturally expresses ferredoxin and ferredoxin reductase. In such a cell, it is not necessary to exogenously introduce a nucleic acid encoding ferredoxin and ferredoxin reductase. However, it is particularly preferred that in such a cell, a nucleic acid encoding ferredoxin and ferredoxin reductase is further introduced, to increase the expression of ferredoxin and ferredoxin reductase, thereby further enhancing the activity of the polypeptide according to the invention. In some cases, the cell does not express ferredoxin and ferredoxin reductase. In such a cell, it is particularly preferred that a nucleic acid encoding ferredoxin and ferredoxin reductase is introduced, so as to provide a high-efficient electron donor for the polypeptide according to the invention.

In some preferred embodiments, DMAPP may be added to a cell culture medium, so as to provide a substrate for the polypeptide according to the invention. In some preferred embodiments, DXP pathway is established in a cell to promote DMAPP synthesis in the cell, thereby providing a substrate for the polypeptide according to the invention. For example, one or more polypeptides involved in DXP pathway can be expressed in a cell to promote DMAPP synthesis in the cell, thereby providing a substrate for the polypeptide according to the invention Therefore, in some preferred embodiments, the cell further expresses a polypeptide of DXP pathway. In some preferred embodiments, the polypeptide of DXP pathway is selected from the group consisting of 1-deoxy-D-xylulose-5-phosphate synthase (DXS; EC 2.2.1.7), 1-deoxy-D-xylulose-5-phosphate reductoisomerase (DXR; EC 1.1.1.267), 2-C-methyl-D-erythritol 4-phosphate cytidylyltransferase (MCT; EC 2.7.7.60), 4-(cytidine-5'-diphospho)-2-C-methyl-D-erythritol kinase (CMK; EC 2.7.1.148), 2-C-methyl-D-erythritol 2,4-cyclodiphosphate synthase (MCS; EC 4.6.1.12), 4-hydroxy-3-methyl-2-(E)-butenyl-diphosphate synthase (IspG; EC 1.17.7.1), and any combination thereof. In some preferred embodiments, the cell expresses one, two, three, four, five or six of said polypeptides of DXP pathways.

In some preferred embodiments, the polypeptide of DXP pathway is endogenous relative to the cell. In some preferred embodiments, the polypeptide of DXP pathway is exogenous relative to the cell.

In some preferred embodiments, the cell further expresses isopentenyl diphosphate isomerase (IDI; EC 5.3.3.2). In some preferred embodiments, the isopentenyl diphosphate isomerase is endogenous relative to the cell. In some preferred embodiments, the isopentenyl diphosphate isomerase is exogenous relative to the cell.

In some preferred embodiments, the cell is selected from the group consisting of a prokaryotic cell such as *E. coli* cell and *bacillus* cell (e.g., *Bacillus alcalophilus, Bacillus subtilis*), and a eukaryotic cell such as a yeast cell, an insect cell, a plant cell and an animal cell. However, it is particularly preferred that the cell is a prokaryotic cell, such as *E. coli* or *Bacillus* spp. or blue-green algae.

In some preferred embodiments, the method is used in biosynthesis of isoamylene (e.g., 3-methyl-1-butene and/or 2-methyl-2-butene).

In another aspect, the invention provides a method for preparing the polypeptide according to the invention, comprising (a) culturing a host cell comprising and expressing a nucleic acid encoding the polypeptide; and (b) collecting the polypeptide expressed by the cell.

A variety of host cells for protein expression are well known by a person skilled in the art, including, but not limited to a prokaryotic cell such as *E. coli* cell, and a eukaryotic cell such as a yeast cell, an insect cell, a plant cell and an animal cell (for example, a mammalian cell, such as a mouse cell and a human cell). It is particularly preferred that the host cell is *E. coli*.

Definition and Explanation of Relevant Terms

In the invention, unless otherwise specified, the scientific and technical terms used herein have the meanings as generally understood by a person skilled in the art. Moreover, the relevant laboratory operating steps as used herein are the conventional steps widely used in the corresponding field. In addition, in order to understand the invention better, definitions and explanations are provided below for relevant terms.

As used herein, the term "HMBPP" refers to 4-hydroxy-3-methyl-but-2-enyl pyrophosphate, the structural formula of which is shown in the following Formula (I):

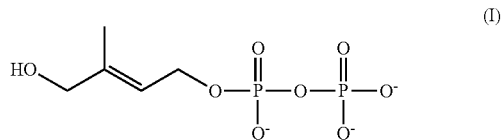

As used herein, the term "DMAPP" refers to dimethylallyl pyrophosphate, the structural formula of which is shown in the following Formula (II):

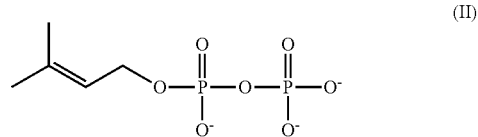

As used herein, the term "2M2B" refers to 2-methyl-2-butene, having a structural formula of

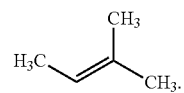

As used herein, the term "3M1B" refers to 3-methyl-1-butene, having a structural formula of

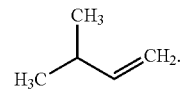

As used herein, the term "isoprene" refers to 2-methyl-1,3-butadiene, having a structural formula of

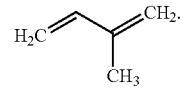

As used herein, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison ×100. For example, if 6 of 10 sites of two sequences are matched, the two sequences have an identity of 60%. For example, DNA sequences, CTGACT and CAGGTT, share an identity of 50% (3 of 6 sites are matched). Generally, the alignment of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" refers to an amino acid substitution which would not disadvantageously affect or change the essential properties of a protein/polypeptide comprising an amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, conservative substitution generally refers to substitution of a corresponding amino acid residue with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl Acad. Set USA 94: 412-417 (1997), which are incorporated herein by reference).

In the application, it has been, demonstrated that IspH protein set forth in SEQ ID NO: 2 can convert HMBPP to isoprene. At the same time, methods for mutating a known polypeptide to obtain its mutant have been described in the prior art in detail, and are exemplarily described in the present application. For example, Examples of the description provide methods for preparing mutants of the IspH protein, and prepare 2 mutants (H131N and E133Q). In addition, methods for determining whether a polypeptide has an activity of converting HMBPP to isoprene are known by a person skilled in the art and are described in detail in the application. For example, Examples of the description provide methods for determining whether H131N and E133Q can use HMBPP as a substrate to produce isoprene, and it has been demonstrated that both H131N and E133Q have the activity of converting HMBPP to isoprene. Therefore, the methods according to the invention can be carried out repeatedly to prepare other mutants of the IspH protein which have the activity of converting HMBPP to isoprene. Therefore, the polypeptides according to the invention are not limited to IspH protein set forth in SEQ ID NO: 2 and its mutants H131N and E133Q, and intend to cover all the other mutants of IspH protein as long as they still retain the activity of converting HMBPP to isoprene.

As used herein, the expression "nucleic, acid/polypeptide is heterogeneous relative to a cell" means that the nucleic acid/polypeptide is not naturally present in the cell. That is, the cell in its natural state does not comprise or express the nucleic acid/polypeptide.

As used herein, the expression "nucleic acid/polypeptide is endogenous relative to a cell" means that the nucleic acid/polypeptide is naturally present in the cell. That is, the cell in its natural state comprises or expresses the nucleic acid/polypeptide.

As used herein, the expression "nucleic acid/polypeptide is exogenous relative to cell" means that the nucleic acid/polypeptide is exogenously introduced into the cell artificially. It should be understood that such a nucleic acid/polypeptide may not be naturally present in the cell (i.e., is heterogenous relative to the cell), and is used to introduce a heterogenous nucleic acid/polypeptide into a cell; or may also be identical to an endogenous nucleic acid/polypeptide that is naturally present in the cell, and is used to increase the copy number or expression of the endogenous nucleic acid/polypeptide in the cell.

As used herein, the term "electron transporter" refers to a protein involved in electron transport in an electron transport chain, in general, an electron transporter can not only accept electrons as an electron acceptor, but also provide electrons as an electron donor, and therefore can achieve electron transport. Such electron transporters are well known by a person skilled in the art, including, but not limited to, ferredoxin and flavodoxin. In addition, the involvement of an oxido-reductase (which is also called an enzyme needed for an electron transporter to transport electron) is generally needed during electron transport by an electron transporter. For example, the involvement of ferredoxin reductase is generally needed in electron transport of ferredoxin; the involvement of flavodoxin reductase is generally needed in electron transport of flavodoxin. An enzyme needed for an electron transporter to transport electron is also well known by a person skilled in the art, for example, including, but not limited to ferredoxin reductase and flavodoxin reductase.

As used herein, the term "ferredoxin reductase" refers to an enzyme capable of catalyzing oxidation-reduction reactions of ferredoxin, including two types:

(1) ferredoxin-$NADP^+$ reductase, which has an IntEnz accession number of EC 1.18.1.2, and can catalyze the following reaction:

2 ferredoxin in reduced form+$NADP^+$+$H^+$ ⇌ 2 ferredoxin in oxidized form+NADPH; and (2) ferredoxin-NAD$^+$ reductase, which has an IntEnz accession number of EC 1.18.1.3, and can catalyze the following reaction:

2 ferredoxin in reduced form+NAD$^+$+H$^+$ ⇌ 2 ferredoxin in oxidized form+NADH.

In the invention, ferredoxin reductase is preferably ferredoxin-NADP$^+$ reductase (EC 1.18.1.2).

As used herein, the term "a polypeptide of DXP pathway" refers to a polypeptide involved in DXP pathway. DXP pathway refers to a pathway of synthesizing DMAPP from pyruvate and glyceraldehyde 3-phosphate as raw materials, comprising the following steps: (1) producing 1-deoxy-D-xylulose 5-phosphate (DXP) by condensation of pyruvate and glyceraldehyde 3-phosphate; (2) converting DXP to 2-C-methyl-D-erythritol 4-phosphate (MEP); (3) converting MEP to 4-(cytidine 5'-diphospho)-2-C-methyl-D-erythritol (CDP-ME); (4) converting CDP-ME to 4-(cytidine 5'-diphospho)-2-C-methyl-D-erythritol 2-phosphate (CDP-ME2P); (5) converting CDP-ME2P to 2-C-methyl-D-erythritol 2,4-cyclodiphosphate (MECDP); (6) converting MECDP to HMBPP; and (7) converting HMBPP to DMAPP and IPP. The detailed description of DXP pathway may be found in, for example, Tomohisa Kuzuyama, Biosci. Biotechnol. Biochem., 66(8), 1619-1627, 2002; Thomas D. Sharkey et al., Plant Physiology, February 2005, Vol. 137, pp. 700-712; and U.S. Pat. No. 8,507,235B2.

The polypeptides involved in DXP pathway include, but are not limited to 1-deoxy-D-xylulose-5-phosphate synthase (DXS; EC 2.2.1.7), 1-deoxy-D-xylulose-5-phosphate reductoisomerase (DXR; EC 1.1.1.267), 2-C-methyl-D-erythritol 4-phosphate cytidylyltransferase (MCT; EC 2.7.7.60), 4-(cytidine-5'-diphospho)-2-C-methyl-D-erythritol kinase (CMK; EC 2.7.1.148), 2-C-methyl-D-erythritol 2,4-cyclodiphosphate synthase (MCS; EC 4.6.1.12), 4-hydroxy-3-methyl-2-(E)-butenyl-diphosphate synthase (IspG; EC 1.17.7.1). The detailed description of these polypeptides (enzymes) can be found in the public database IntEnz (http://www.ebi.ac.uk/intenz/).

As used herein, the term "isoprene synthase (IspS)" refers to an enzyme capable of using DMAPP as a substrate to produce isoprene, which has an IntEnz accession number of EC 4.2.3.27.

As used herein, the term "isopentenyl diphosphate isomerase (IDI)" refers to an enzyme capable of catalyzing the isomerization between DMAPP and IPP, also called IPP isomerase, which has an IntEnz accession number of EC 5.3.3.2.

Beneficial Technical Effects of the Invention

The polypeptide (enzyme) according to the invention can use HMBPP as a substrate to produce isoprene directly. Compared to the method and enzyme for producing isoprene based on the MEP pathway, the technical solutions of the invention have the following beneficial effects:

(1) DMAPP is not involved in the method for producing isoprene according to the invention, thereby avoiding accumulation of DMAPP and IPP in a host cell, which is toxic to the growth of the host cell; and (2) in the method for producing isoprene according to the invention, one enzymatic reaction is omitted, and isoprene synthase (IspS) is not involved, thereby simplifying the process and increasing the efficiency.

The embodiments of the invention are illustrated in detail by reference to the following drawings and examples. However, it is understood by those skilled in the art that the following drawings and examples are used only for the purpose of illustrating the invention, rather than limiting the protection scope of the invention. Based on the following detailed description of the drawings and the preferred embodiments, the purposes and the beneficial aspects of the invention are obvious for a person skilled in the art.

Figure 9:
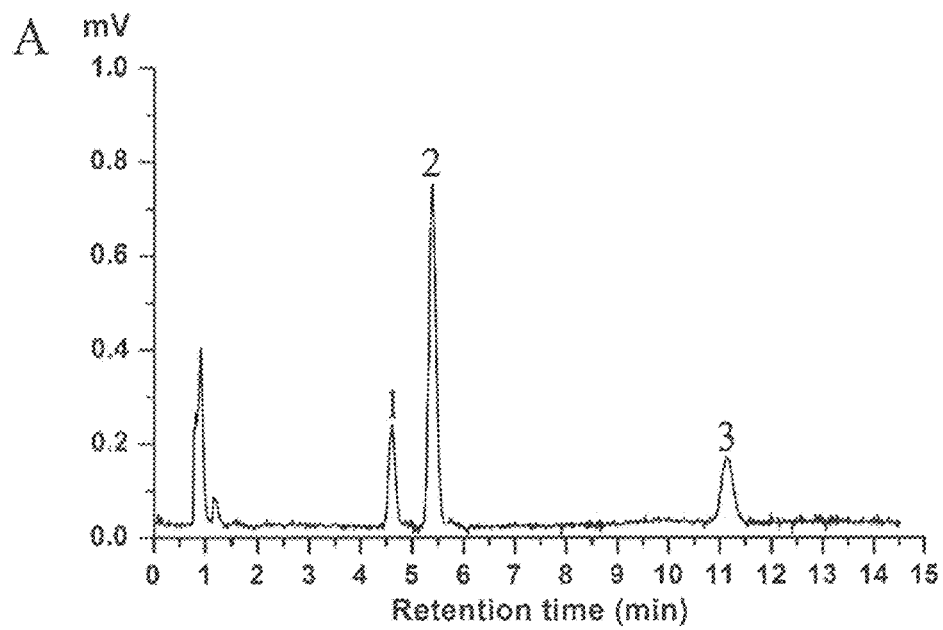
FIG. 9 shows the GC characteristic spectrum of the headspace gas of the cultured recombinant *E. coli* cell STV165HF (FIG. 9A), and GC characteristic spectrum of the standard substances (3-methyl-1-butene, 2-methyl-2-butene, 2-methyl-1-butene and isoprene) (FIG. 9B), wherein the GC conditions used are: an injection port temperature of 180° C., a column temperature of 100° C., and a detector temperature of 200° C.; Peak a is the characteristic peak of 3-methyl-1-butene; Peak b is the characteristic peak of 2-methyl-2-butene; Peak c is the characteristic peak of 2-methyl-1-butene; and Peak d is the characteristic peak of isoprene.
Figure 9:
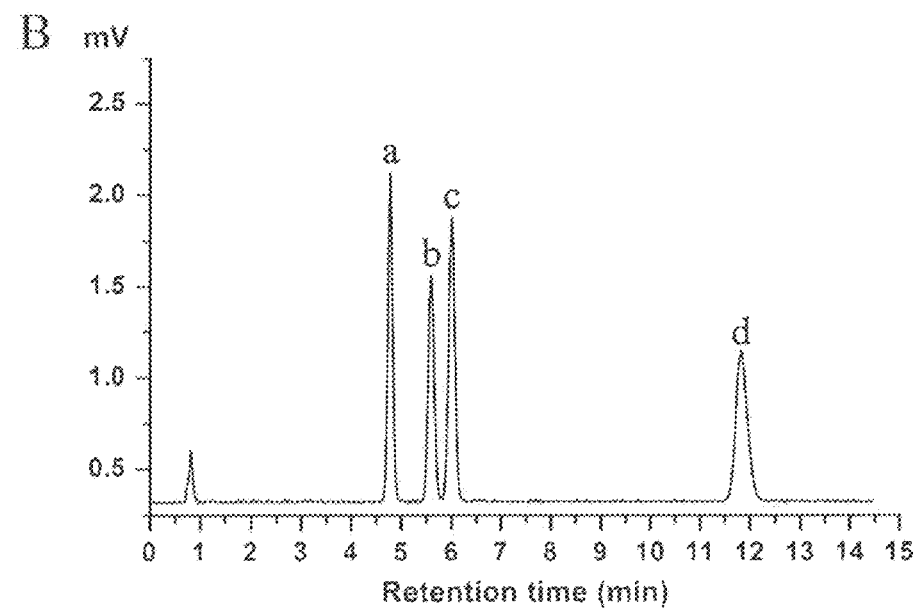
Figure 10:
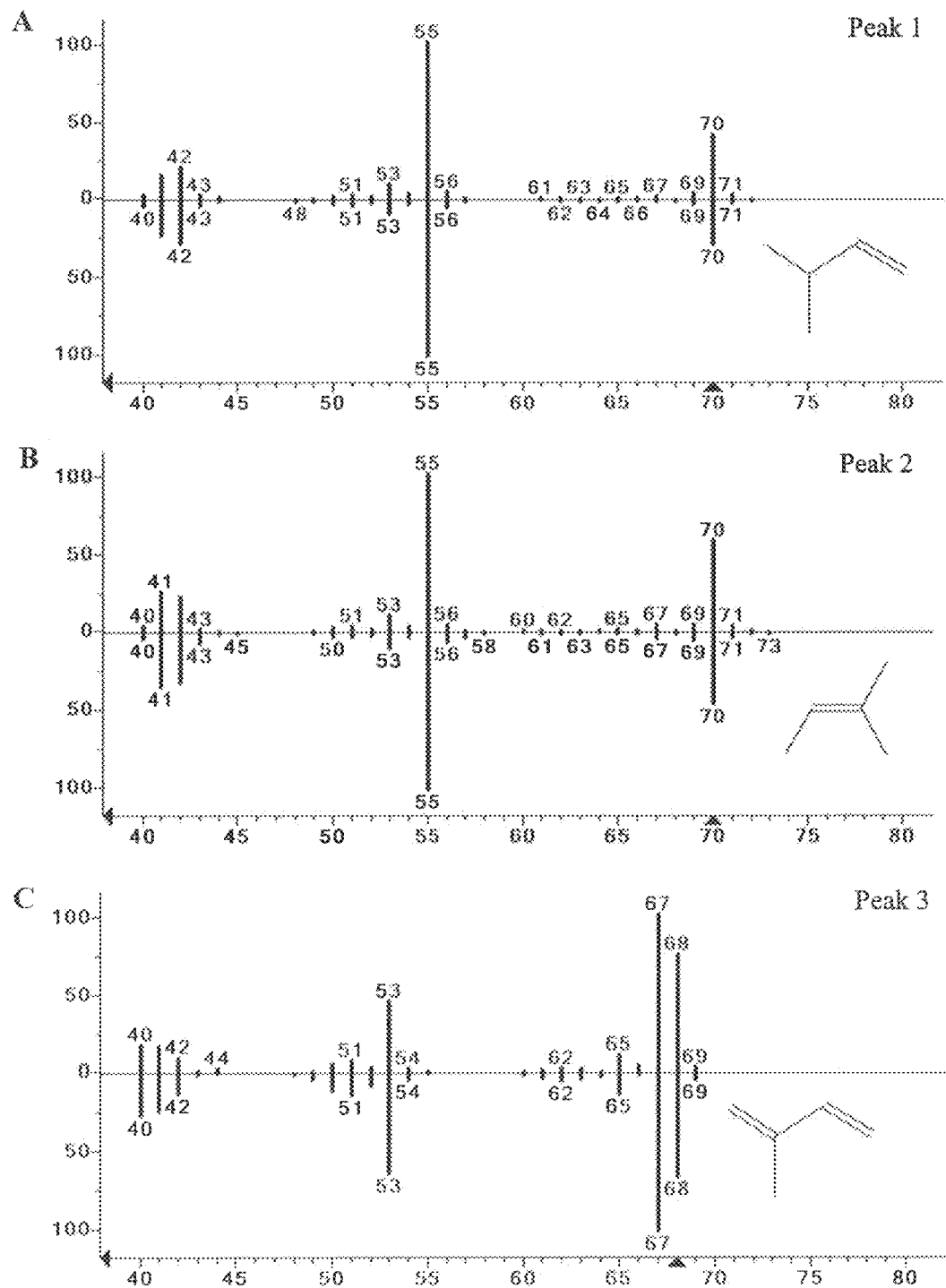
FIG. 10 shows the comparison of MS analytic results between Peak 1 component of FIG. 9A and the standard substance 3-methyl-1-butene (FIG. 10A), between Peak 2 component of FIG. 9A and the standard substance 2-methyl-2-butene (FIG. 10B), and between Peak 3 component of FIG. 9A and the standard substance isoprene (FIG. 10C): wherein in FIGS. 10A-10C, the figures above the abscissa show the MS analytic results of the components to be tested (Peak 1, Peak 2, Peak 3), while the figures below the abscissa show the MS analytic results of the standard substances (3-methyl-1-butene, 2-methyl-2-butene, isoprene).

The experimental results of FIGS. 9-10 show that the recombinant *E. coli* cell STV165HF overexpressing IspH protein can produce significant amounts of isoprene (Peak 3), 2-methyl-2-butene (Peak 2) and 3-methyl-1-butene (Peak 1).

Figure 11:
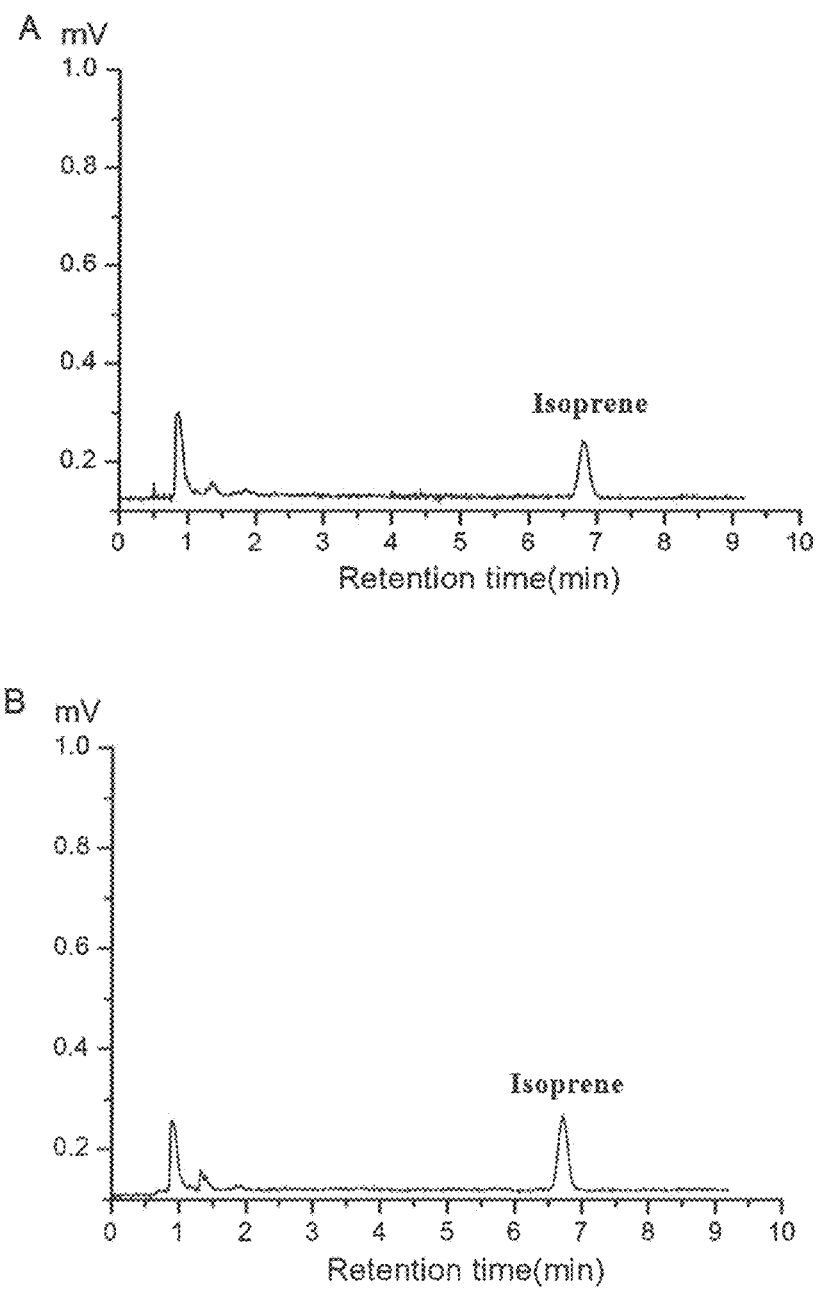

FIG. 11 shows the GC characteristic spectrum of the headspace gas of the cultured recombinant *E. coli* cells STV165HF-H131N (FIG. 11A) and STV165HF-E133Q (FIG. 11B); wherein the GC conditions used are: an injection port temperature of 180° C., a column temperature of 130° C. and a detector temperature of 200° C.; and it is identified by mass spectrum analysis that the headspace gas detected in FIGS. 11A-11B contains isoprene, but no isoamylene. These experimental results show that the recombinant *E. coli* cells over-expressing the mutant protein H131N or E133Q can produce significant amounts of isoprene, but no isoamylene.

SEQUENCE INFORMATION

The information of sequences involved in the invention is provided in the following Table 1.

TABLE 1

Description of sequences

| SEQ ID NO: | Description |
|---|---|
| 1 | nucleotide sequence of IspH gene from alkaliphlic *Bacillus* sp. N16-5 |
| 2 | amino acid sequence of IspH protein from alkaliphilic *Bacillus* sp. N16-5 |
| 3 | amino acid sequence of the mutant protein H131N |
| 4 | amino acid sequence of the mutant protein E133Q |
| 5 | primer |
| 6 | primer |
| 7 | primer |
| 8 | primer |
| 9 | primer |
| 10 | primer |

Sequence 1 (SEQ ID NO: 1):

```
atggaggttttgaaaatttccccacggggttattgttccggcgtggtagatgctatggtt      60 atggctaaacaagctgctgaaaatccagatttaccacggcctatctatatattaggaatg     120 attgttcacaataaacatgtgacagatgcctttgatgaagagggtattatcacgcttgac    180
```

TABLE 1-continued

Description of sequences

| | |
|---|---|
| ggtccaaacagattagagattattaagcaagttgataaaggauccgttattttacggca | 240 |
| catggcgtttcgccegaagtacgaactatcgctaaagaaaaaggattaacgacgatcgat | 300 |
| gccacatgtccagatgtaaccgtcactcacgacctaattcgaaataaaatggaagagggc | 360 |
| tacgagtttatctacattggtaagaaaggacaccccgagccagaaggcgctatcggtgtt | 420 |
| gctccagacattgtttatttagtagaaaatgttgaagatgtagaaagacttcagctgaaa | 480 |
| ggcaataaaattcttataacaaaccagacgacaatgagtcaatgggatgtctctcacatc | 540 |
| attaaagctgcgaaaaacaaatacctgaagcagaggtccataacgaaatttgcatggct | 600 |
| actcaagttcgtcaagaagctgttgctgaacaagctggagaagctgatttactaattgtt | 660 |
| gtgggtgatccgaaaagtaataactctaatcgtctcgcacaagtatcgatggacattacc | 720 |
| ggaacacctgcctacagaatagcaaatgttaatgaactcaatcttgaatggcttaaaggg | 780 |
| atcaaaaaagtggcagtcactgctggggctagcacacccactcctgttacaaaagaagtg | 840 |
| attgctttcatcgaaaagtttaatgaagatgaccccacacatgggatacgacgagtact | 900 |
| gttaaattaacaaaaattctccctaaagtgagaaagaaaaaagcggagcgggcctaa | 957 |

Sequence 2 (SEQ ID NO: 2):
MEVLKISPRGYCYGVVDAMVMAKQAAENPDLPRPIYILGMIVHNKHVTDAFDEEGHTLDGPNRLEIIK

QVDKGTVIFTAHGVSPEVRTIAKEKGLTTIDATCPDVTVTHDLIRNKMEEGYEFIYGKKGPEPEGAIG

VAPDIVYLVENVEDVERLQLKGNKILITNQTTMSQWDVSHIIKAAKNKYPEAEVHNEICMATQVRQE

AVAEQAGEADLLIVVGDPKSNNSNRLAQVSMDITGTPAYRIANVNELNLEWLKGIKKVAVTAGASTP

TPVTKEVIAFIEKFNEDDPHTWDTTSTVKLTKILPKVRKKKAERA

Sequence 3 (SEQ ID NO: 3):
MEVLKISPRGYCYGVVDAMVMAKQAAENPDLPRPIYILGMIVHNKHVTDAFDEEGHTLDGPNRLEIIK

QVDKGTVIFTAHGVSPEVRTIAKEKGLTTIDATCPDVTVTHDLIRNKMEEGYEFIYIGKKGNPEPEGAIG

VAPDIVYLVENVEDVERLQLKGNKILITNQTTMSQWDVSHIIKAAKNKYPEAEVHNEICMATQVRQE

AVAEQAGEADLLIVVGDPKSNNSNRLAQVSMDITGTPAYRIANVNELNLEWLKGIKKVAVTAGASTP

TPVTKEVIAFIEKFNEDDPHTWDTTSTVKLTKILPKVRKKKAERA

Sequence 4 (SEQ ID NO: 4):
MEVLKISPRGYCYGVVDAMVMAKQAAENPDLPRPIYILGMIVHNKHVTDAFDEEGHTLDGPNRLEIIK

QVDKGTVIFTAHGVSPEVRTIAKEKGLTTIDATCPDVTVTHDLIRNKMEEGYEFIYIGKKGHPQPEAKAI

GVAPDIVYLVENVEDVERLQLKGNKILITNQTTMSQWDVSHIIKAAKNKYPEAEVHNEICMATQVRQ

EAVAEQAGEADLLIVVGDPKSNNSNRLAQVSMDITGTPAYRIANVNELLNLEWLKGIKKVAVTAGAST

PTPVTKEVIAFIEKFNEDDPHTWDTTSTVKLTKILPKVRKKKAERA

Sequence 5 (SEQ ID NO: 5):
CATGCCATGGAGGTTTTGAAAATTTCC

Sequence 6 (SEQ ID NO: 6):
CCGCTCGAGTGGCCCGCTCCGCTTTTTTCTTTC

Sequence 7 (SEQ ID NO: 7):
CTACATTGGTAAGAAAGGAAACCCCGAGCCAGAAGGCG

Sequence 8 (SEQ ID NO: 8):
CGCCTTCTGGCTCGGGGTTCCTTTCTTACCAATGTAG

Sequence 9 (SEQ ID NO: 9):
GTAAGAAAGGACACCCCCAGCCAGAAGGCGCTATC

Sequence 10 (SEQ ID NO: 10):
GATAGCGCCTTCTGGCTGGGGGTGTCCTTTCTTAC

Specific Modes for Carrying Out the Invention

The present invention is described by reference to the following examples which are used to illustrate the invention rather than limiting the present invention.

Unless specified otherwise, the molecular biological experimental methods used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; the detection methods used are the conventional detection methods in the art, which are carried out in accordance with the steps described in the relevant literatures or the steps recommended by manufacturers of devices used herein. Those skilled in the art understand that the examples are used for illustrating the invention, but not intended to limit the protection scope of the invention.

Example 1. Gene Cloning

Alkaliphilic *Bacillus* sp. N16-5 (*Bacillus* sp. N16-5) (obtained from China General Microbiological Culture Collection Center, CGMCC) was cultured in Horikoshi-I medium containing 2% NaCl (pH 10.0) (see, Horikoshi K., Microbiol Mol Biol Rev. 1999; 63:735-50). DNA Isolation Kit (E.Z.N.A.™ Bacterial DNA Isolation Kit, Omega, USA) was used to isolate the genomic DNA of alkaliphilic *Bacillus* sp. N16-5. PCR amplification was carried out by using the isolated genomic DNA as a template, and the following primers: upstream primer 275F: 5"-CATG CCATGGAGGTTTTGAAAATTTCC-3" (SEQ ID NO: 5), wherein the underlined portion indicates the NcoI restriction site; and downstream primer 275R: 5'-CCG CTCGAGTGGCCCGCTCCGCTTTTTTCTTTC-3' (SEQ ID NO: 6), wherein the underlined portion indicates the XhoI restriction site. PCR reaction system was 50 µL, and the reaction conditions were: pre-denaturation at 94° C. for 3 min; 30 cycles of (denaturation at 94° C. for 1 min, annealing at 58° C. for 30 s, and extension at 72° C. for 1.5 min); and extension at 72° C. for 5 min.

PCR products were purified by the kit (E.Z.N.A.™ Bacterial DNA isolation Kit, Omega, USA), cleaved by the enzymes NcoI and XhoI, and then ligated to the vector pET28a (TaKaRa Co.) which has been cleaved by the enzymes NcoI and XhoI, and finally transformed into *E. coli* DH5α. In LB medium, the transformed *E. coli* DH5α was cultured, and the plasmid was extracted therefrom. The plasmid was verified by sequencing. The sequencing results show that the gene (IspH gene) inserted into the vector pET28a has the sequence set forth in SEQ ID NO: 1, and the protein (IspH protein) encoded thereby has an amino acid sequence set forth in SEQ ID NO: 2. The constructed plasmid was designated as pET-H.

Example 2. Expression and Purification of Polypeptide

The protein encoded by isc (iron-sulfur cluster) operon of *E. coli* facilitates the correct formation of [4Fe-4S] center of the IspH protein according to the invention. Therefore, in order to make the expressed IspH protein have a high activity, firstly, isc operon is highly expressed in *E. coli*. In brief, the isc operon is ligated to the vector pSTV28, and then is transformed into *E. coli* BL21 (DE), in order to increase the copy number of the operon in the host cell, and to enhance the expression of the protein encoded by operon (Grawert, T. et al. IspH protein of *Escherichia coli*: studies on iron-sulfur cluster implementation and catalysis. Journal of the American Chemical Society 126, 12847-12855 (2004)). Later, the pET-H plasmid constructed above is transformed into the *E. coli* highly expressing isc operon.

The transformed *E. coli* was cultured in LB medium containing 25 mg/L chloramphenicol and 50 mg/L kanamycin, and cultured at 37° C. until the OD value was about 0.6. Later, cysteine (1 mM), $FeCl_3$ (0.1 mM) and 0.1 mM IPTG were added to the culture, and the host cell was further cultured at 18° C. under low-speed oscillation for 16 h. After the culturing was finished, the bacteria were collected by centrifugation, washed with distilled water twice, and stored at −80° C. for later use.

The protein expressed in the bacteria was purified under anaerobic conditions. In brief, the collected bacteria were lysed with BugBuster Protein Extraction Reagent (Merck, Germany). Later, the bacterial lysate was centrifuged at 16000 g for 20 min, the supernatant was collected, and the precipitate was discarded. Since the expressed IspH protein has a 6*His-tag at the amino terminal (the 6*His-tag was encoded by the sequence carried by the pET28a vector itself, and was located at N terminal of the protein expressed by the recombinant vector), in accordance with the instructions of the manufacturer, Ni-NTA column (Merck, Germany) and a desalting column (Sangon Biotech, China) were used to purify the IspH protein in the supernatant. The purified IspH protein was brown, and was stored at −80° C. for later use.

In addition, by similar methods, ferredoxin and ferredoxin-NADP$^+$ reductase (FNR) were expressed and purified. In brief, the DNA fragments encoding ferredoxin and ferredoxin-NADP$^+$ reductase were separately cloned to the vector pET28a, and then transformed into *E. coli* and expressed. Later, *E. coli* was lysed, and the proteins expressed in *E. coli* were purified by using Ni-NTA column (Merck, Germany) and a desalting column (Sangon Biotech, China). The purified ferredoxin and ferredoxin-NADP$^+$ reductase were separately stored at −80° C. for later use.

Figure 1:
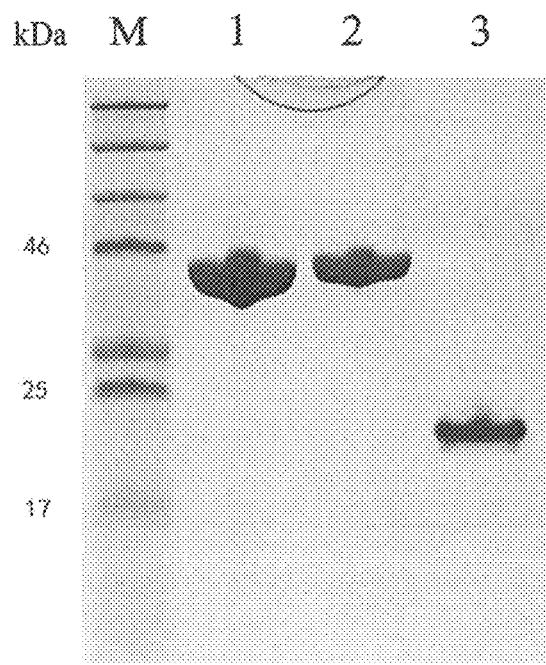
FIG. 1 shows the SDS-PAGE detection results of the proteins expressed and purified in Example 2, wherein, Lane M: molecular weight marker; Lane 1: ferredoxin-NADP$^+$ reductase: Lane 2: IspH protein; Lane 3: ferredoxin. The results show that the IspH protein according to the invention can be expressed at a high level in *E. coli*, has a molecular weight of about 35 kD, and has a high purity after purification, as indicated in the single electrophoresis band in Lane 2 of FIG. 1. In addition, the results of FIG. 1 also show that by the method of Example 2, highly pure ferredoxin (a molecular weight of about 11 kD, as shown in the single electrophoresis band in Lane 3 of FIG. 1) and ferredoxin-NADP$^+$ reductase (a molecular weight of about 36 kD, as shown in the single electrophoresis band in Lane 1 of FIG. 1) were obtained.

The purified proteins were determined by SDS-PAGE. The results were shown in FIG. 1. The results show that the IspH protein according to the invention can be expressed at a high level in *E. coli*, has a molecular weight of about 35 kD, and has a high purity after purification, as indicated in the single electrophoresis band in Lane 2 of FIG. 1. Similarly, the results of FIG. 1 also show that by the above method, highly pure ferredoxin (having a molecular weight of about 11 kD, as indicated in the single electrophoresis band in Lane 3 of FIG. 1) and ferredoxin-NADP$^+$ reductase (having a molecular weight of about 36 kD, as indicated in the single electrophoresis band in Lane 1 of FIG. 1) were obtained.

Figure 2:
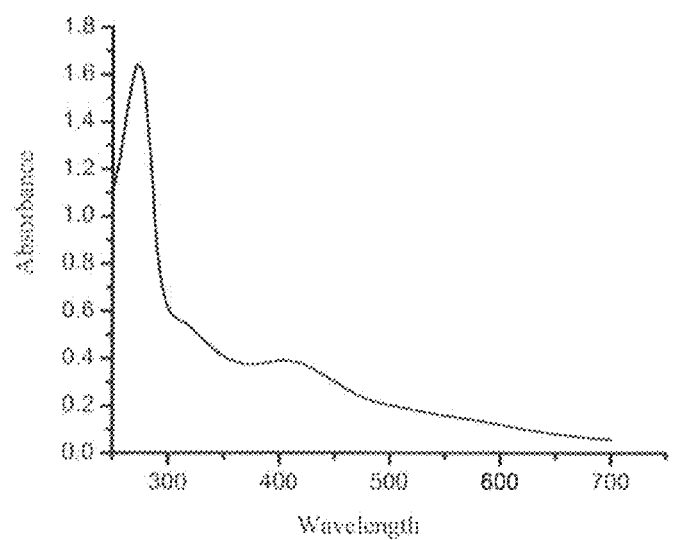
FIG. 2 shows the full-wavelength broad-spectrum scan results of the purified IspH protein, wherein, the abscissa represents wavelength, and the ordinate represents absorbance. The results show that the IspH protein according to the invention has a maximum absorption peak at 410 nm and a shoulder peak at 320 nm. This indicates that the protein contains an iron-sulfur center.

In addition, the purified IspH protein was subjected to the full-wavelength broad-spectrum scan. The results were shown in FIG. 2. The results of FIG. 2 show that the IspH protein according to the invention has a maximum absorption peak at 410 nm and a shoulder peak at 320 nm. This indicates that the protein contains an iron-sulfur center.

Example 3. Preparation of IspH Mutants

By means of site-directed mutagenesis, two mutants of IspH protein, H131N and E133Q, were prepared, wherein, the mutant H131N (with a sequence set forth in SEQ ID NO: 3) differs from IspH protein by mutation of histidine to asparagine at position 131 of SEQ ID NO: 2; and the mutant E133Q (with a sequence set forth in SEQ ID NO: 4) differs from IspH protein by mutation of glutamic acid to glutamine at position 133 of SEQ ID NO: 2.

In brief, whole plasmid PGR was carried out by using the plasmid pET-H as a template, and the following primers:

```
The primer pair for constructing the mutant H131N:
H131N-F:
                                         (SEQ ID NO: 7)
CTACATTGGTAAGAAAGGAaACCCCGAGCCAGAAGGCG H131N-R:
                                         (SEQ ID NO: 8)
CGCCTTCTGGCTCGGGGTtTCCTTTCTTACCAATGTAG;

The primer pair for constructing the mutant E133Q:
E133Q-F:
                                         (SEQ ID NO: 9)
GTAAGAAAGGACACCCCcAGCCAGAAGGCGCTATC, E133Q-R:
                                         (SEQ ID NO: 10)
GATAGCGCCTTCTGGCTgGGGGTGTCCTTTCTTAC
```

The amplification product was treated with DpnI enzyme at 37° C. for 2 h, and then transformed into E. coli DMT strain (TransGen Biotech). In LB medium, the transformed E. coli DMT was cultured, and the plasmid was extracted therefrom. The plasmid was verified by sequencing. Later, the plasmid having a correct sequence was transformed into E. coli highly expressing isc operon, to express the mutant protein. The mutant proteins were expressed and purified by the methods described in Example 2.

Figure 3:
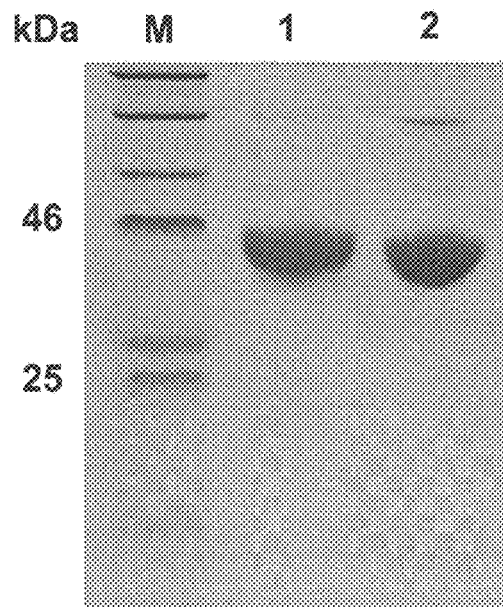
FIG. 3 shows the SDS-PAGE electrophoresis results of the mutant proteins H131N and E133Q expressed and purified in Example 3, wherein Lane M: molecular weight marker; Lane 1: mutant protein H131N; Lane 2: mutant protein E133Q. The results show that the mutant proteins H131N and E133Q according to the invention can be expressed at high levels in *E. coli*, have a molecular weight of about 35 kD, and have a high purity after purification.

The purified mutant proteins H131N and E133Q were determined by SDS-PAGE. The results were shown in FIG. 3. The results show that the mutant proteins H131N and E133Q according to the invention can be expressed at high levels in E. coli, have a molecular weight of about 35 kD, and have a high purity after purification.

Example 4. Determination of In Vitro Activity (1) Activity Assay Using HMBPP as a Substrate Under anaerobic conditions, in a sealed 5 ml chromatotube, IspH protein and its mutants were determined for their activity, wherein the reaction system comprised: 150 mM NaCl, 20 mM Tris-HCl (pH 7.8), 2 mM DTT, 1 mM NADPH, 1 mM HMBPP, 20 μM ferredoxin, 5 μM ferredoxin-NADP$^+$ reductase, and 0.5 μM IspH protein or its mutants (H131N and E133Q) obtained above; the total reaction volume was 500 μl; and the reaction condition was incubation at 37° C. for 1 h.

After the reaction, the headspace gas in the chromatotube was collected, and was subjected to gas chromatography-mass spectrometry (GC-MS). In brief, the gas was analyzed by Agilent Technologies 7890B GG/5977A MSD equipped with Agilent HP-PLOT Al2O3/S GC column (25 m, 0.32 mm, 8.00 μm, 7 inch cage), wherein He gas was used as a carrier gas at a flow rate of 2 ml/min. Later, the experimental data of the test sample (peak retention time, peak area, mass spectrogram, etc.) was compared with the experimental data of the standard substance (isoprene, 3-methyl-1-butene and 2-methyl-2-butene) to identify the gas components and perform quantitative analysis.

In addition, after the reaction, the reaction solution in the chromatotube was also analyzed to determine whether IPP and DMAPP were produced. Since DMAPP can spontaneously produce isoprene under acidic conditions, the amount of DMAPP in the reaction solution can be determined by determining the amount of isoprene produced in the reaction solution under acidic conditions. In brief, under anaerobic conditions, 50 μL reaction solution was put in another 5 ml chromatotube, and diluted with cold water to a volume of 500 μL, and an equal volume of 8M $H_2SO_4$ was added; then, the chromatotube was sealed immediately, and incubated at 37° C. for 30 min. After the incubation, the amount of isoprene in the headspace gas was determined by the above-mentioned GC-MS method, to determine whether the reaction solution contained DMAPP or not.

The experimental results were shown in Table 2. The results show that both the wild-type IspH protein and its mutants (H131N and E133Q) can catalyze the conversion of HMBPP to isoprene, and they are not significantly different from each other in terms of catalytic ability. In addition, the results also show that in the reaction system containing the wild-type IspH protein, isoamylene (3-methyl-1-butene and 2-methyl-2-butene) is produced; while in the reaction systems containing the mutant proteins (H131N and E133Q), the production of isoamylene was not detected. In addition, the results also show that in the reaction solution containing the wild-type IspH protein, isoprene was produced under acidic conditions (which indicates the presence of DMAPP in the reaction system); in contrast, in the reaction solutions containing the mutant proteins (H131N and E133Q), isoprene was not produced substantively under acidic conditions (which indicates that DMAPP is not present in the reaction system substantively).

TABLE 2

Quantitative analysis of headspace gas in the reaction system and the headspace gas of the reaction solution treated with acid

|  | wild-type IspH | IspH-H131N | IspH-E133Q |
| --- | --- | --- | --- |
| Isoprene (μg L$^{-1}$ OD$^{-1}$) produced in the reaction system | 104.4 | 100.2 | 106.4 |
| Production of 3-methyl-1-butene or not | yes | no | no |
| Production of 2-methyl-2-butene or not | yes | no | no |
| isoprene (μg L$^{-1}$ OD$^{-1}$) produced by treating the reaction solution with acid | 696.3 | 10.0 | 6.1 |

The results show that the wild-type IspH can use HMBPP as a substrate to produce isoprene, isoamylene, IPP and DMAPP; in contrast, the mutant proteins H131N and E133Q can only catalyze the conversion of HMBPP to isoprene, and cannot produce isoamylene, IPP and DMAPP substantively.

(2) Activity Assay Using DMAPP/IPP as a Substrate

Under anaerobic conditions, in a sealed 5 ml chromatotube, IspH protein and its mutants were determined for their activity, wherein the reaction system comprised: 150 mM NaCl, 20 mM Tris-HCl (pH 7.8), 2 mM DTT, 1 mM NADPH, 1 mM DMAPP, 20 μM ferredoxin, 5 μM ferredoxin-NADP$^+$ reductase, and 0.5 μM IspH protein or its mutants (H131N and E133Q) obtained above; the total reaction volume was 500 μl; and the reaction condition was incubation at 37° C. for 1 h.

After the reaction, the headspace gas in the chromatotube was collected, and was subjected to gas chromatography-mass spectrometry (GC-MS). The experimental results show that the wild-type IspH protein uses DMAPP substrate to produce isoamylene, i.e., 2-methyl-2-butene and 3-methyl-1-butene (at a ratio of about 7:1-8:1). In contrast, the mutant proteins H131N and E133Q lose the activity, and are unable to convert DMAPP to isoamylene.

In addition, IPP was used as a substrate to repeat the experiment. The experimental results show that none of the wild-type IspH protein and the mutant proteins (H131N and E133Q) has a catalytic activity on IPP.

Figure 4:
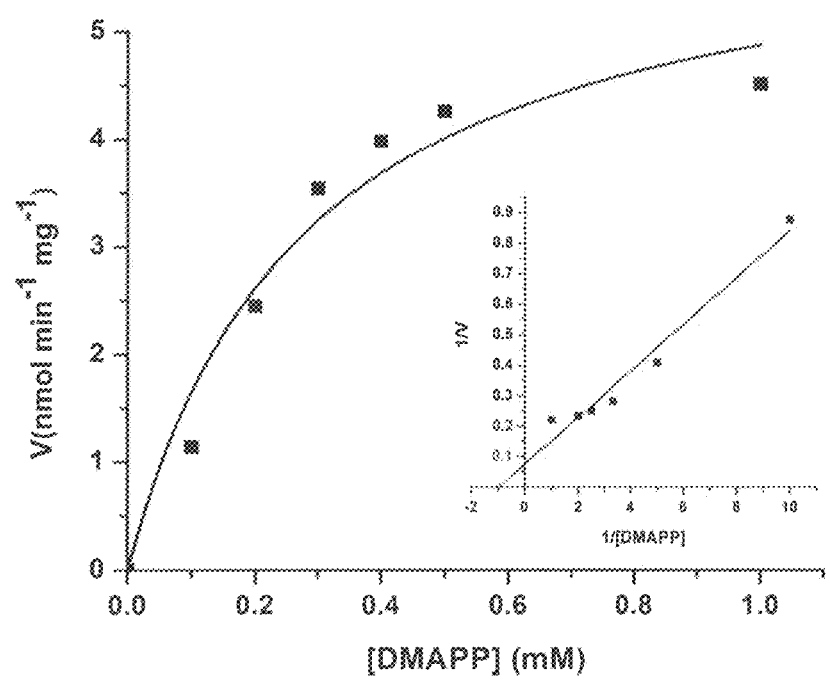
FIG. 4 shows the Michaelis-Menten curve of the enzymatic reaction of converting DMAPP to isoamylene by IspH protein, wherein, the abscissa represents the DMAPP concentration (mM), and the ordinate represents the reaction rate (nmol min$^{-1}$ mg$^{-1}$). The panel in FIG. 4 shows the Lineweaver-Burk curve of the enzymatic reaction, wherein the abscissa represents the reciprocal value of the DMAPP concentration, and the ordinate represents the reciprocal valise of the reaction rate. The results show that the wild-type IspH protein has a maximum reaction activity of about 6.2 nmol min$^{-1}$ mg$^{-1}$, and a Km value of about 275 μM, when using DMAPP as a substrate to produce isoamylene.

In order to determine the kinetic parameters of the wild-type IspH protein, DMAPP at different concentrations (0, 0.1, 0.2, 0.3, 0.4, 0.5, 1.0 mM) was used to repeat the experiment. The experimental results are shown in FIG. 4. The experimental results show that the wild-type IspH protein has a maximum reaction activity of about 6.2 nmol min$^{-1}$ mg$^{-1}$, and Km of about 275 µM, when using DMAPP as a substrate to produce isoamylene.

In order to further determine whether the wild-type IspH protein in assay (1) uses HMBPP or DMAPP as a substrate to produce isoamylene, the reaction system containing the wild-type IspH protein were determined for the components in the headspace gas, in different phases of the assay (1). The results show that in early phase of the reaction, the headspace gas of the reaction system only contains isoprene, and no isoamylene (2-methyl-2-butene and 3-methyl-1-butene). As the reaction proceeds, the headspace gas of the reaction system begins to contain isoamylene. The experimental results show that (i) the wild-type IspH protein can convert HMBPP to isoprene; and (ii) the wild-type IspH protein does not have the activity of converting HMBPP to isoamylene directly; however, it can convert HMBPP to DMAPP, and further convert DMAPP to isoamylene.

Figure 5:
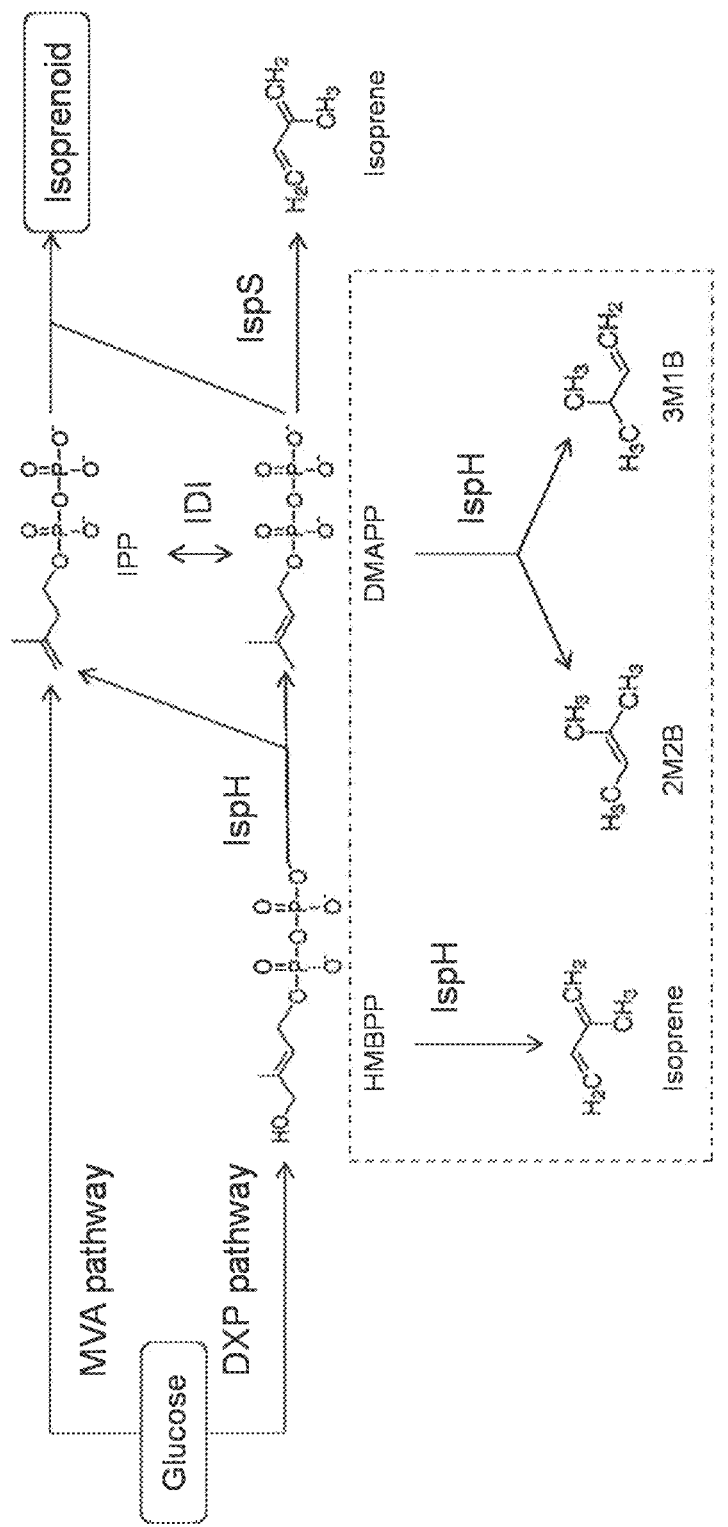
FIG. 5 shows the schematic diagram on the three activities of the IspH protein of the invention, wherein, HMBPP: 4-hydroxy-3-methyl-but-2-enyl pyrophosphate; DMAPP: dimethylallyl pyrophosphate; IPP: isopentenyl pyrophosphate; IDI: isopentenyl diphosphate isomerase; IspS: isoprene synthase; 2M2B: 2-methyl-2-butene; 3M1B: 3-methyl-1-butene.

In view of the experimental results above, the wild-type IspH protein according to the invention has three catalytic activities (FIG. 5): (a) using HMBPP as a substrate to produce DMAPP and IPP; (h) using HMBPP as a substrate to produce isoprene; and (c) using DMAPP as a substrate to produce isoamylene (2-methyl-2-butene and 3-methyl-1-butene). In contrast, the mutant proteins H131N and E133Q only retain the activity of using HMBPP as a substrate to produce isoprene, and substantively lose the other activities (i.e., can neither convert HMBPP to IPP and DMAPP substantively, nor convert DMAPP to 2-methyl-2-butene and 3-methyl-1-butene).

Example 5. Determination of Intracellular Activity

The alkaliphilic *Bacillus* sp. N16-5 strain, from which the IspH protein according to the invention was derived, was selected as a host cell, and IspH protein and its mutants (H131N and E133Q) were over-expressed therein, and the gas produced by the host cell was detected to determine the intracellular activity of the IspH protein and its mutants.

In brief, the DNA fragment encoding IspH protein or its mutant (H131N or E133Q) was fused to pLDH (lactate dehydrogenase promoter), and cloned to the vector pMK4, so as to construct an expression vector. Later, the constructed expression vector was transformed into alkaliphilic *Bacillus* sp. N16-5 by protoplast-transformation method, to construct a recombinant host cell. By the method above, three recombinant cells as following were constructed: the recombinant cell WNH, which was the alkaliphilic *Bacillus* sp. N16-5 overexpressing the wild-type IspH protein; the recombinant cell H131N, which was the alkaliphilic *Bacillus* sp. N16-5 overexpressing the mutant H131N; and the recombinant cell E133Q, which was the alkaliphilic *Bacillus* sp. N16-5 overexpressing the mutant E133Q.

The constructed recombinant cells were seeded to the sealed culture bottles, and cultured at 37° C. for 12 h. Later, 1 mL headspace gas in the culture bottles was then subjected to GC-MS analysis. The detailed methods for GC-MS analysis are as described above. In addition, the wild-type alkaliphilic *Bacillus* sp. N16-5 (WT) was used as a control.

Figure 6:
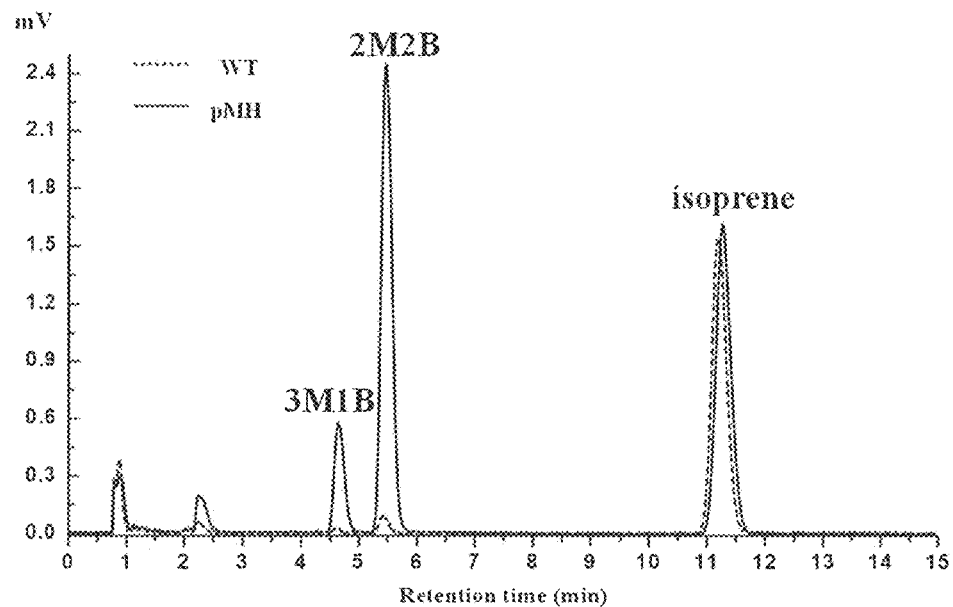
FIG. 6 shows the GC characteristic spectrum of the headspace gas of the cultured wild-type alkaliphilic *Bacillus* sp. N16-5 (WT) and the recombinant cell WNH (pMH), wherein 3-methyl-1-butene (3M1B), 2-methyl-2-butene (2M2B) and isoprene have a retention time of 4.5 mm, 5.5 min, and 11.3 min, respectively. The results show that the wild-type alkaliphilic *Bacillus* sp. N16-5 can produce isoprene, and insignificant amounts of 2-methyl-2-butene and 3-methyl-1-butene; and the recombinant cell WNH overexpressing IspH protein has the yield of 2-methyl-2-butene and 3-methyl-1-butene improved significantly, but has the yield of isoprene improved slightly.
Figure 7:
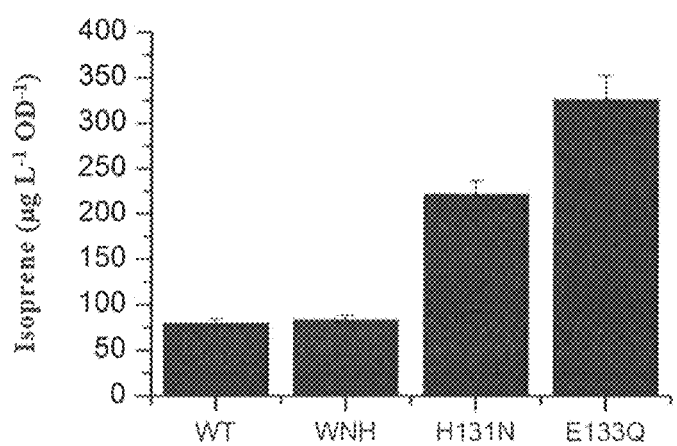
FIG. 7 shows the comparison of the isoprene yield among the wild-type alkaliphilic *Bacillus* sp. N16-5 (WT), and the recombinant cells WNH, H131N and E133Q. The results show that compared to the wild-type alkaliphilic *Bacillus* sp. N16-5, the recombinant cell WNH has the isoprene yield improved slightly, but the recombinant cells H131N and E133Q have the isoprene yields improved significantly, which are 3 folds and 4 folds of the yield in the wild-type bacterial strain, respectively.

The experimental results are shown in FIGS. 6-7 and Table 3. FIG. 6 shows the GC characteristic spectrum of the headspace gas of the cultured wild-type alkaliphilic *Bacillus* sp. N16-5 (WT) and recombinant cell WNH (pMH), wherein 3-methyl-1-butene (3M1B), 2-methyl-2-butene (2M2B) and isoprene have a retention time of 4.5 min, 5.5 min, and 11.3 min, respectively. The results show that the wild-type alkaliphilic *Bacillus* sp. N16-5 can produce isoprene, and insignificant amounts of 2-methyl-2-butene and 3-methyl-1-butene; and the recombinant cell WNH overexpressing the wild-type IspH protein has the yield of 2-methyl-2-butene and 3-methyl-1-butene improved significantly, but has the yield of isoprene improved slightly. In addition, the results also show that the isoamylene yield of the recombinant cells H131N and E133Q are not significantly changed as compared to that of the wild-type alkaliphilic *Bacillus* sp, N16-5 (Table 3).

FIG. 7 shows the comparison of the isoprene yield among the wild-type alkaliphilic *Bacillus* sp. N16-5 (WT) and the recombinant cells WNH, H131N and E133Q. The results show that compared to wild-type alkaliphilic *Bacillus* sp. N16-5, the recombinant cell WNH has the isoprene yield improved slightly, but the recombinant cells H131N and E133Q have the isoprene yields improved significantly, which are about 3 folds and 4 folds of the yield in the wild-type bacterial strain, respectively.

Table 3 shows comparison of the isoamylene yield and isoprene yield among the wild-type alkaliphilic *Bacillus* sp. N16-5 (WT) and the recombinant cells WNH, H131N and E133Q. The results show that compared to the wild-type alkaliphilic *Bacillus* sp, N16-5, the recombinant cell WNH has the isoamylene yield improved significantly, and the isoprene yield improved slightly; the recombinant cells H131N and E133Q have the isoprene yield improved significantly (which are about 3 folds and 4 folds of the yield in the wild-type bacterial strain, respectively), but have no significant change in the isoamylene yield.

TABLE 3

Comparison of the isoamylene yield and isoprene yield among the strains

| Strain | Isoamylene yield (µg L$^{-1}$ OD$^{-1}$) | | | Isoprene yield (µg L$^{-1}$ OD$^{-1}$) | | |
| --- | --- | --- | --- | --- | --- | --- |
| WT | 3 | 3 | 3 | 79 | 75 | 85 |
| WNH | 65 | 68 | 78 | 82 | 78 | 89 |
| H131N | 3 | 3 | 3 | 224 | 206 | 236 |
| E133Q | 3 | 3 | 3 | 297 | 311 | 350 |

Figure 8:
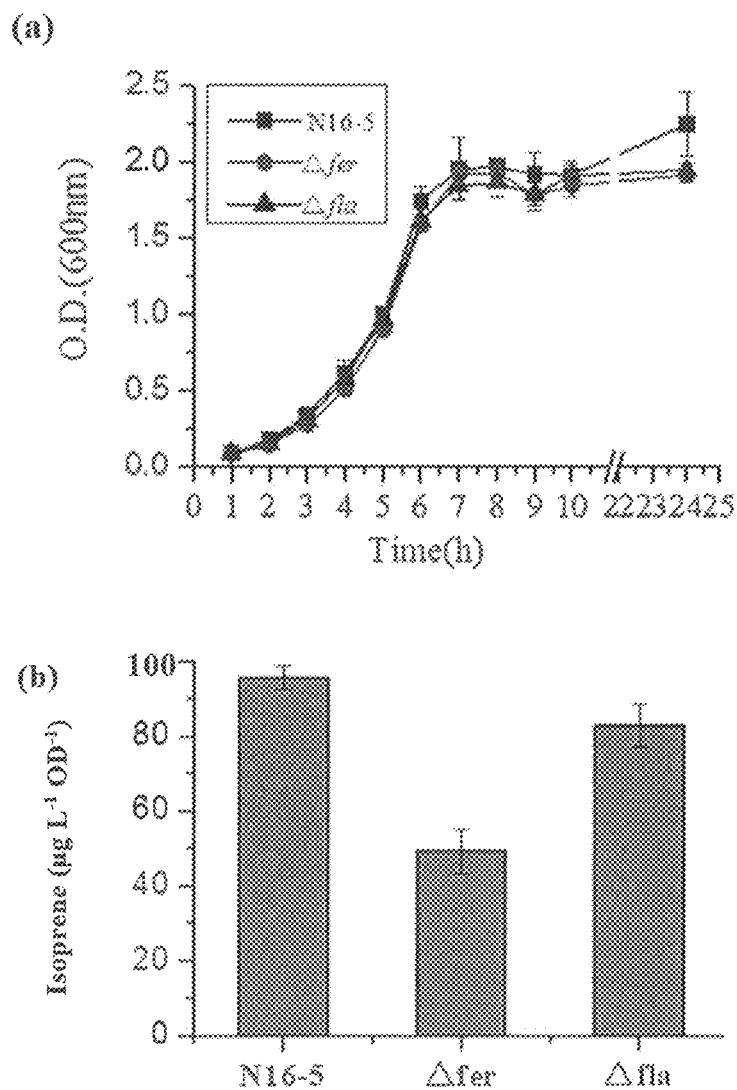
FIG. 8a shows the growth of the wild-type strain and the mutant strains Δfer and Δfld of alkaliphilic *Bacillus* sp. N16-5. The results show that all the three strains can grow normally in Horikoshi-I medium, and are not significantly different from each other in terms of growth.
FIG. 8b shows the comparison of the isoprene yield among the wild-type strain and the mutant strains Δfer and Δfld of alkaliphilic *Bacillus* sp. N16-5. The results show that the isoprene yield of the mutant strain Δfer (which is only about 50% of that of the wild-type strain) is significantly lower than that of the wild-type strain; while the isoprene yield of the mutant strain Δfld is slightly lower than that of the wild-type strain. These experimental results show that both ferredoxin and flavodoxin can be used as electron donors needed for IspH protein to produce isoprene (i.e., when ferredoxin is absent, flavodoxin can be used as electron donor; and vice versa); however, ferredoxin is more preferred and more efficient for the catalytic activity of IspH protein.

In addition, alkaliphilic *Bacillus* sp. N16-5 can express the electron transporters, ferredoxin and flavodoxin. In order to observe the dependency of IspH protein activity on the two electron transporters, two mutant strains of alkaliphilic *Bacillus* sp. N16-5 were prepared: Δfer, deficiency in fer gene encoding ferredoxin; and Δfld, deficiency in fld gene encoding flavodoxin. The two mutant strains were cultured, and were compared to the wild-type alkaliphilic *Bacillus* sp. N16-5 in terms of growth and isoprene yield. The experimental results are shown in FIG. 8.

FIG. 8a shows the growth of the wild-type strain and the mutant strains Δfer and Δfld of alkaliphilic *Bacillus* sp. N16-5. The results show that all the three strains can grow normally in Horikoshi-I medium, and are not significantly different from each other in terms of growth. FIG. 8b shows the comparison of the isoprene yield among the wild-type strain and the mutant strains Δfer and Δfld of alkaliphilic *Bacillus* sp. N16-5. The results show that the isoprene yield of the mutant strain Δfer is significantly lower than that of the wild-type strain, (which is only about 50% of that of the wild-type strain); while the isoprene yield of the mutant strain Δfld is slightly lower than that of the wild-type strain. These experimental results show that both ferredoxin and flavodoxin can be used as electron donors for IspH protein to produce isoprene (i.e., when ferredoxin is absent, flavodoxin can be used as electron donor; and vice versa); however, ferredoxin is more preferred and more efficient for the catalytic activity of IspH protein.

In addition, *E. coli* was used to determine the intracellular activity of IspH protein and its mutants (H131N and E133Q).

In brief, the DNA fragments encoding IspH protein and ferredoxin were cloned to the vector pSTV28, to construct the expression vector pSTV165HF. Later, the constructed expression vector was transformed into *E. coli* Trans 109 strain (TransGen Biotech), to construct the recombinant cell STV165HF, which was *E. coli* overexpressing IspH protein and ferredoxin.

In addition, by a similar method, the recombinant cell STV165HF-H131N was constructed, which was *E. coli* overexpressing the mutant protein H131N and ferredoxin; and the recombinant cell STV165HF-E133Q was constructed, which was *E. coli* overexpressing the mutant protein E133Q and ferredoxin.

The constructed recombinant cells were seeded to the sealed culture bottles, and cultured at 37° C. for 10 h. 1 mL headspace gas in the culture bottles was then subjected to GC-MS analysis. The detailed method for GC-MS analysis was as described above.

The experimental results are shown in FIGS. 9-11. FIG. 9 shows the GC characteristic spectrum of the headspace gas of the cultured recombinant *E. coli* cell STV165HF (FIG. 9A), and GC characteristic spectrum of the standard substances (3-methyl-1-butene, 2-methyl-2-butene, 2-methyl-1-butene and isoprene) (FIG. 9B), wherein the GC conditions used are: an injection port temperature of 180° C., a column temperature of 100° C., and a detector temperature of 200° C.; and Peak a is the characteristic peak of 3-methyl-1-butene; Peak b is the characteristic peak of 2-methyl-2-butene; Peak c is the characteristic peak of 2-methyl-1-butene; and Peak d is the characteristic peak of isoprene.

FIG. 10 shows the comparison of MS analytic results between Peak 1 component of FIG. 9A and the standard substance 3-methyl-1-butene (FIG. 10A), between Peak 2 component of FIG. 9A and the standard substance 2-methyl-2-butene (FIG. 10B), and between Peak 3 component of FIG. 9A and the standard substance isoprene (FIG. 10C); wherein in FIGS. 10A-10C, the figures above the abscissa show the MS analytic results of the components to be tested (Peak 1, Peak 2, Peak 3), while the figures below the abscissa show the MS analytic results of the standard substances (3-methyl-1-butene, 2-methyl-2-butene, isoprene).

The experimental results of FIGS. 9-10 show that the recombinant *E. coli* cell STV165HF overexpressing IspH protein can produce significant amounts of isoprene (Peak 3), 2-methyl-2-butene (Peak 2) and 3-methyl-1-butene (Peak 1).

FIG. 11 shows the GC characteristic spectrum of the headspace gas of the cultured recombinant *E. coli* cells STV165HF-H131N (FIG. 11A) and STV165HF-E133Q (FIG. 11B); wherein the GC conditions used are: an injection port temperature of 180° C. a column temperature of 130° C., and a detector temperature of 200° C. Furthermore, the components of the peaks in FIGS. 11A-11B are identified by mass spectrum analysis. The results show that the headspace gas detected in FIGS. 11A-11B contains isoprene, but no isoamylene. Therefore, these experimental results show that the recombinant *E. coli* cells overexpressing the mutant protein H131N or E133Q can produce significant amounts of isoprene, but no isoamylene.

The experimental results show that the IspH protein and its mutants according to the invention can be used to construct recombinant engineering bacteria capable of biosynthesizing isoprene. In addition, the IspH protein according to the invention can also be used to construct recombinant engineering bacteria capable of biosynthesizing isoamylene (2-methyl-2-butene and 3-methyl-1-butene).

Although the embodiments of the invention have been described in detail, a person skilled in the art would understand that according to all the disclosed teachings, details can be amended and modified, and these changes all fall into the protection scope of the invention. The scope of the invention is defined by the attached claims and any equivalent thereof.

The invention claimed is:

1. A polypeptide, which has an activity of using 4-hydroxy-3-methyl-but-2-enyl pyrophosphate (HMBPP) as a substrate to produce isoprene, and has an amino acid sequence selected from the group consisting of:

(1) an amino acid sequence set forth in SEQ ID NO: 2;

(2) an amino acid sequence having an identity of at least 95%, an identity of at least 96%, an identity of at least 97%, an identity of at least 98%, or an identity of at least 99% with SEQ ID NO: 2;

(3) an amino acid sequence that differs from SEQ ID) NO: 2 by substitution, deletion or addition of 1, 2, 3, 4, 5, 6, 7, 8 or 9 amino acid residues, optionally, the polypeptide also has an activity of using dimethylallyl pyrophosphate (DMAPP) as a substrate to produce 2-methyl-2-butene and 3-methyl-1-butene, and (4) wherein each of the amino acid sequences of (1), (2) and (3) has an amino acid substitution at position 131 or 133 of the sequence of SEQ ID NO: 2.

2. An isolated nucleic acid, encoding the polypeptide according to claim 1.

3. A vector comprising the isolated nucleic acid according to claim 2.

4. A cell comprising (i) the isolated nucleic acid according to claim 2 and/or (ii) a vector comprising the isolated nucleic acid, wherein the isolated nucleic acid is heterogenous or exogenous relative to the cell;
    optionally, the cell further comprises a nucleic acid encoding an electron transporter and/or an enzyme needed for an electron transporter to transport electron, or expresses an electron transporter and/or an enzyme needed for an electron transporter to transport electron.

5. A composition, comprising the polypeptide according to claim 1, HMBPP, NADPH or NADH, an electron transporter, and an enzyme needed for an electron transporter to transport electron.

6. A composition, comprising the polypeptide according to claim 1, DMAPP, NADPH or NADH, an electron transporter, and an enzyme needed for an electron transporter to transport electron, wherein the polypeptide has an amino acid sequence set forth in SEQ ID NO: 2.

7. A method for producing isoprene, comprising using the polypeptide according to claim 1 to convert HMBPP to isoprene;
    wherein the method comprises, (a) mixing and incubating the polypeptide, HMBPP, NADPH or NADH, an electron transporter and an enzyme needed for an electron transporter to transport electron; and (b) collecting isoprene produced in step (a).

8. A method for producing isoprene, comprising, (a) culturing a cell expressing the polypeptide according to claim 1 which is exogenously introduced; and, (b) collecting isoprene produced in step (a);
    optionally, the cell further expresses an electron transporter, and/or an enzyme needed for an electron transporter to transport electron, and/or a polypeptide of DXP pathway.

9. A method for producing isoamylene, comprising using the polypeptide according to claim 1 to convert DMAPP to isoamylene; wherein, the polypeptide has an amino acid sequence set forth in SEQ ID NO: 2;
    wherein the method comprises, (a) mixing and incubating the polypeptide, DMAPP, NADPH or NADH, an electron transporter and an enzyme needed for an electron transporter to transport electron; and (b) collecting isoamylene produced in step (a).

10. A method for producing isoamylene, comprising: (a) culturing a cell expressing the polypeptide according to claim 1 which is exogenously introduced, wherein the polypeptide has an amino acid sequence set forth in SEQ ID NO: 2, and (b) collecting isoamylene produced in step (a);
    optionally, the cell further expresses an electron transporter, and/or an enzyme needed for an electron transporter to transport electron, and/or a polypeptide of DXP pathway, and/or isopentenyl diphosphate isomerase (IDI; EC 5.3.3.2).

11. A method for preparing the polypeptide according to claim 1, comprising (a) culturing a host cell comprising and expressing a nucleic acid encoding the polypeptide; and (b) collecting the polypeptide expressed by the cell.

12. The polypeptide according to claim 1, wherein the amino acid sequence of the polypeptide is SEQ ID NO: 2 or differs from SEQ ID NO: 2 by substitution of 1 amino acid residues.

13. The polypeptide according to claim 1, wherein the polypeptide has an amino acid sequence selected from the group consisting of SEQ ID NOs: 2, 3 and 4.

14. The cell according to claim 4, wherein the cell further comprises a nucleic acid encoding ferredoxin and ferredoxin reductase, or expresses ferredoxin and ferredoxin reductase.

15. The cell according to claim 4, wherein the cell further expresses a polypeptide of DXP pathway.

16. The cell according to claim 15, wherein the polypeptide of DXP pathway is selected from the group consisting of 1-deoxy-D-xylulose-5-phosphate synthase (DXS; EC 2.2.1.7), 1-deoxy-D-xylulose-5-phosphate reductoisomerase (DXR; EC 1.1.1.267), 2-C-methyl-D-erythritol 4-phosphate cytidylyltransferase (MCT; EC 2.7.7.60), 4-(cytidine-5'-diphospho)-2-C-methyl-D-erythritol kinase (CMK; EC 2.7.1.148), 2-C-methyl-D-erythritol 2,4-cyclodiphosphate synthase (MCS; EC 4.6.1.12), 4-hydroxy-3-methyl-2-(E)-butenyl-diphosphate synthase (IspG; EC 1.17.7.1), and any combination thereof.

17. The cell according to claim 4, wherein the cell is a prokaryotic cell, e.g., *E. coli* or *Bacillus* spp. or blue-green algae.

18. The composition according to claim 5, wherein the composition comprises the polypeptide, HMBPP, NADPH, ferredoxin and ferredoxin reductase.

19. The composition according to claim 6, wherein the composition comprises the polypeptide, DMAPP, NADPH, ferredoxin and ferredoxin reductase.

* * * * *